(12) United States Patent
Tearney et al.

(10) Patent No.: US 12,178,596 B2
(45) Date of Patent: *Dec. 31, 2024

(54) APPARATUS, METHODS AND COMPUTER-ACCESSIBLE MEDIA FOR IN SITU THREE-DIMENSIONAL RECONSTRUCTION OF LUMINAL STRUCTURES

(71) Applicant: The General Hospital Corporation, Boston, MA (US)

(72) Inventors: Guillermo J. Tearney, Cambridge, MA (US); Joseph A. Gardecki, Acton, MA (US); Kanwarpal Singh, Weymouth, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/484,155

(22) Filed: Oct. 10, 2023

(65) Prior Publication Data

US 2024/0032855 A1 Feb. 1, 2024

Related U.S. Application Data

(63) Continuation of application No. 17/849,072, filed on Jun. 24, 2022, now Pat. No. 11,813,068, which is a
(Continued)

(51) Int. Cl.
*A61B 5/00* (2006.01)
*A61B 8/08* (2006.01)
(Continued)

(52) U.S. Cl.
CPC .............. *A61B 5/42* (2013.01); *A61B 5/0084* (2013.01); *A61B 5/0093* (2013.01);
(Continued)

(58) Field of Classification Search
CPC ....... A61B 5/42; A61B 5/0084; A61B 5/0093; A61B 8/5261; A61B 2562/0266; G06T 17/00
See application file for complete search history.

(56) References Cited

U.S. PATENT DOCUMENTS 9,255,853 B2  2/2016 Weisman
2006/0253942 A1  11/2006 Barrera
(Continued)

FOREIGN PATENT DOCUMENTS

JP  2014-115219 A  6/2014
RU  2485562 C1  6/2013
(Continued)

OTHER PUBLICATIONS

European Patent Office. Extended European Search Report and Written Opinion, Application No. 18770191.7, Jan. 19, 2021, 8 pages.
(Continued)

*Primary Examiner* — Rochelle D Turchen
(74) *Attorney, Agent, or Firm* — Quarles & Brady LLP

(57) ABSTRACT

An apparatus for determining a shape of a luminal sample including: a catheter including a lens, the catheter disposed within a strain-sensing sheath such that the lens rotates and translates; a structural imaging system optically coupled to the catheter; a strain-sensing system optically coupled to the catheter; and a controller coupled to the strain-sensing system and the structural imaging system. The controller determines: a first position of the catheter relative to the luminal sample at a first location within the strain-sensing sheath; a second position of the catheter relative to the luminal sample at a second location within the strain-sensing sheath; a first strain of the strain-sensing sheath at the first location; a second strain of the strain-sensing sheath at the second location; a local curvature of the luminal sample
(Continued)

relative to the catheter; a local curvature of the catheter; and a local curvature of the luminal sample.

19 Claims, 16 Drawing Sheets

Related U.S. Application Data continuation of application No. 16/496,204, filed as application No. PCT/US2018/024014 on Mar. 23, 2018, now Pat. No. 11,406,318.

(60) Provisional application No. 62/475,304, filed on Mar. 23, 2017.

(51) Int. Cl.
 *G06T 17/00* (2006.01)
 *A61B 8/12* (2006.01)

(52) U.S. Cl.
 CPC ............ *A61B 8/5261* (2013.01); *G06T 17/00* (2013.01); *A61B 8/12* (2013.01); *A61B 2562/0266* (2013.01)

(56) References Cited

U.S. PATENT DOCUMENTS

| | | |
|---|---|---|
| 2009/0177095 A1 | 7/2009 | Aeby |
| 2009/0264768 A1 | 10/2009 | Courtney et al. |
| 2013/0334541 A1 | 12/2013 | Voss et al. |
| 2014/0230562 A1 | 8/2014 | Yamamoto et al. |
| 2014/0275986 A1 | 9/2014 | Vertikov |
| 2015/0245881 A1 | 9/2015 | Larkin et al. |
| 2015/0272442 A1 | 10/2015 | Motafakker-Fard et al. |
| 2016/0262784 A1 | 9/2016 | Grace et al. |
| 2016/0374562 A1 | 12/2016 | Vertikov |

FOREIGN PATENT DOCUMENTS

| | | |
|---|---|---|
| WO | 2011098926 A1 | 8/2011 |
| WO | 2012101562 A1 | 8/2012 |
| WO | 2016194059 A1 | 12/2016 |

OTHER PUBLICATIONS

European Patent Office, Communication Pursuant to Article 94(3) EPC, Application No. 18770191.7, Jul. 14, 2023, 4 pages.
Japan Patent Office. Notification of Reasons for Refusal, Application No. 2019-5552205, March, 8, 2022, 7 pages.
Japan Patent Office, Notification of Reasons for Refusal, Application No. 2023-000384, Nov. 21, 2023, 5 pages.
Adjedj J, et al. Significance of Intermediate Values of Fractional Flow Reserve in Patients With Coronary Artery Disease. Circulation. 2016; 133(5):502-8. PubMed PMID: 26733607.
Adler J, et al. Quantifying colocalization by correlation: the Pearson correlation coefficient is superior to the Mander's overlap coefficient. Cytometry A. 2010;77(8):733-42. PubMed PMID: 20653013.
Ali Za, et al. Optical coherence tomography compared with intravascular ultrasound and with angiography to guide coronary stent implantation {Ilumien Iii: Optimize Pci): a randomised controlled trial. Lancet. 2016;388 (10060):2618-28. PubMed PMID: 27806900.
Athanasiou LS, et al. 3D reconstruction of coronary arteries using Frequency Domain Optical Coherence Tomography images and biplane angiography. 2012 Annual International Conference of the IEEE Engineering in Medicine and Biology Society; 2012. Aug. 28, 2012-Sep. 1, 2012.
Blachutzik F,et al. Optical coherence tomography: influence of contrast concentration on image quality and diagnostic confidence. Heart Vessels. 2016. PubMed PMID: 27830336.
Bornhoeft LR, et al. Teslaphoresis of Carbon Nanotubes. ACS Nano. 2016; 10(4):4873 81. PubMed PMID: 27074626.
Bourantas CV, et al. A new methodology for accurate 3 dimensional coronary artery reconstruction using routine intravascular ultrasound and angiographic data: implications for widespread assessment of endothelial shear stress in humans. EuroIntervention : journal of EuroPCR in collaboration with the Working Group on Interventional Cardiology of the European Society of Cardiology. 2013;9(5):582-93. PubMed PMID: 23608530.
Bourantas CV, et al. Impact of local endothelial shear stress on neointima and plaque following stent implantation in patients with ST-elevation myocardial infarction: A subgro~p-analysis of the Comfortable AMI IBIS 4 trial. Int J Cardiol. 2015; 186:178-85. PubMed PMID: 25828109.
Calvert PA, et al. Association between IVUS findings and adverse outcomes in patients with coronary artery disease: the VIVA (VH-IVUS in Vulnerable Atherosclerosis) Study. JACC Cardiovasc Imaging. 2011 ;4(8):894-901. PubMed PMID: 21835382.
Cassese S, et al. Prognostic role of restenosis in 10 004 patients undergoing routine control angiography after coronary stenting. Eur Heart. J. 2015;36(2):94-9. PubMed PMID: 25298237.
Chatzizisis YS, et al. Association of global and local low endothelial shear stress with high-risk plaque using intracoronary 3D optical coherence tomography: Introduction of 'shear stress score'. Eur Heart J Cardiovasc Imaging. 2016. PubMed PMID: 27 461211.
Chatzizisis YS, et al. Augmented expression and activity of extracellular matrix-degrading enzymes in regions of low endothelial shear stress colocalize with coronary atheromata with thin fibrous caps in pigs. Circulation. 2011; 123 (6):621-30. PubMed PMID: 21282495; PubMed Central PMCID: PMCPMC3066078.
Chatzizisis YS, et al. Prediction of the localization of high-risk coronary atherosclerotic plaques on the basis of low endothelial shear stress: an intravascular ultrasound and histopathology natural history study. Circulation. 2008; 117 (8):993-1002. PubMed PMID: 18250270.
Chatzizisis YS, et al. Role of endothelial shear stress in the natural history of coronary atherosclerosis and vascular remodeling: molecular, cellular, and vascular behavior. J Am Coll Cardiol. 2007;49(25):2379-93. PubMed PMID: 17599600.
Chen ZJ, et al. A coupled pressure-based computational method for incompressible/compressible flows. Journal of Computational Physics. 2010;229(24 ):9150-65.
Coskun AU, et al. Reproducibility of coronary lumen, plaque, and vessel wall reconstruction and of endothelial shear stress measurements in vivo in humans. Catheterization and cardiovascular interventions : official journal of the Society for Cardiac Angiography & Interventions. 2003;60(1 ):67-78. PubMed PMID: 12929106.
Davies PF, et al. Shear stress biology of the endothelium. Ann Biomed Eng. 2005;33(12):1714-8. PubMed PMID: 16389518.
De Bruyne B, et al. Fractional flow reserve guided PCI for stable coronary artery disease. N Engl J Med. 2014;371 (13):1208-17. PubMed PMID: 25176289.
Depta JP, et al. Outcomes of coronary stenoses deferred revascularization for borderline versus non borderline fractional flow reserve values. Am J Cardiol. 2014; 113(11 ): 1788-93. Pub Med PMID: 24837255.
Dilmen, Nevit, Coronary CTA Model. 2016. Available from: https://3dprint.nih.gov/discover/3DPX-003333.
Ditzel J, et al. Whole-blood viscosity, hematocrit and plasma protein in normal subjects at different ages. Acta Physiol Scand. 1971 ;81 (2):264-8. PubMed PMID: 4101667.
Doulaverakis C, et al: IVUSAngio Tool: A publicly available software for fast and accurate 3D reconstruction of coronary arteries. Computers in Biology and Medicine, 43(11 ): 1793-1803.
Epstein AJ, et al. Coronary revascularization trends in the UnitedStates, 2001-2008. JAMA. 2011 ;305(17): 1769-76. PubMed PMID: 21540420; PubMed Central PMCID: PMCPMC3164857.
Fearon WF. Percutaneous coronary intervention should be guided by fractional flow reserve measurement. Circulation. 2014; 129(18):1860-70. PubMed PMID: 24799502.
Feldman CL, et al. Determination of in vivo velocity and endothelial shear stress patterns with phasic flow in human coronary arteries: a methodology to predict progression of coronary atherosclerosis. American heart journal. 2002; 143 (6):931-9. PubMed PMID:12075241.

(56) References Cited

OTHER PUBLICATIONS

Fihn SD, et al. 2014 ACC/AHA/AATS/PCNA/SCAI/STS focused update of the guideline for the diagnosis and management of patients with stable ischemic heart disease: a report of the American College of Cardiology/American Heart Association Task Force on Practice Guidelines, and the American Association for Thoracic Surgery, Preventive Cardiovascular Nurses Association, Society for Cardiovascular Angiography and Interventions, and Society of Thoracic Surgeons. Circulation. 2014;130(19):1749-67. PubMed PMID: 25070666.
Flavel BS, et al. Separation of single-walled carbon nanotubes with a gel permeation chromatography system. ACS Nano. 2014;8(2): 1817-26. PubMed PMID: 24460395.
Gershlick AH, et al. Randomized trial of complete versus lesion-only revascularization in patients undergoing primary percutaneous coronary intervention for STEMI and multivessel disease: the CvLPRIT trial. J Am Coll Cardiel. 2015;65(10):963-72. PubMed PMID: 25766941; PubMed Central PMCID: PMCPMC4359051.
Giannopoulos AA, et al. Erosion of Thin-Cap Fibroatheroma in an Area of Low Endothelial Shear Stress: Anatomy and Local Hemodynamic Environment Dictate Outcomes. JACC Cardiovasc Interv. 2016;9(8):e77-8. PubMed PMID: 27017369.
Gimbrone MA, Jr., et al. Endothelial dysfunction, hemodynamic forces, and atherogenesis. Ann NY Acad Sci. 2000;902:230-9; discussion 9-40. PubMed PMID: 10865843.
Giraldo JP, et al. A Ratiometric Sensor Using Single Chirality Near-Infrared Fluorescent Carbon Nanotubes: Application to In Vivo Monitoring. Small. 2015; 11 (32):3973-84.
Granada JF, et al. Porcine models of coronary atherosclerosis and vulnerable plaque for imaging and interventional research. EuroIntervention : journal of EuroPCR in collaboration with the Working Group on Interventional Cardiology of the European Society of Cardiology. 2009;5(1 ):140-8. PubMed PMID: 19577996.
Han JH, et al. A mechanochemical model of growth termination in vertical carbon nanotube forests. ACS Nano. 2008;2(1 ):53-60. PubMed PMID: 1920654 7.
Han M, et al. GPU-accelerated framework for intracoronary optical coherence tomography imaging at the push of a button. PLoS One. 2015; 10(4 ):e0124192. PubMed PMID: 25880375; PubMed Central PMCID: PMCPMC4400174.
Hetterich H, et al. Coronary computed tomography angiography based assessment of endothelial shear stress and its association with atherosclerotic plaque distribution in-vivo. PLoS One. 2015; 10(1 ):e0115408. PubMed PMID: 25635397; PubMed Central PMCID: PMCPMC4312082.
Hoogendoorn A, et al. OCT-measured plaque free wall angle is indicative for plaque burden: overcoming the main limitation of OCT? Int J Cardiovasc Imaging. 2016;32(10):1477-81. PubMed PMID: 27437923; PubMed Central PMCID: PMCPMC5021720.
Hu S, et al. Plaque erosion: in vivo diagnosis and treatment guided by optical coherence tomography. JACC Cardiovasc Interv. 2014;7(6):e63-4. PubMed PMID: 24947729.
Huang D, et al: Optical coherence tomography. Science 1991, 254(5035): 1178-1181.
International Searching Authority, International Search Report and Written Opinion for application PCT/US2018/024014, mailed on Jun. 22, 2018, 9 pages.
Jamil Z, et al. Interstudy reproducibility of the second generation, Fourier domain optical coherence tomography in patients with coronary artery disease and comparison with intravascular ultrasound: a study applying automated contour detection. Int J Cardiovasc Imaging. 2013;29(1 ):39-51. PubMed PMID: 22639296; PubMed Central PMCID: PMCPMC3550705.
KIM J-h, et al. Optimization of compute unified device architecture for real-time ultrahigh-resolution optical coherence tomography. Optics Communications. 2015;334:308-13.
Kim TS, et al. Single cardiac cycle three-dimensional intracoronary optical coherence tomography. Biomed Opt Express. 2016;7(12):4847-58. PubMed PMID: 2801871 O; PubMed Central PMCID: PMCPMC5175536.
Koskinas KC, et al. Natural history of experimental coronary atherosclerosis and vascular remodeling in relation to endothelial shear stress: a serial, in vivo intravascular ultrasound study. Circulation. 2010; 121(19):2092-2101. PubMed PMID: 20439786; PubMed Central PMCID: PMCPMC2902864.
Koskinas KC, et al. Role of endothelial shear stress in stent restenosis and thrombosis: pathophysiologic mechanisms and implications for clinical translation. J Am Coll Cardiol.2012;59(15):1337-49. PubMed PMID: 22480478.
Koskinas KC, et al. Thin-capped atheromata with reduced collagen content in pigs develop in coronary arterial regions exposed to persistently low endothelial shear stress. Arterioscler Thromb Vase Biol. 2013;33(7):1494-504. PubMed PMID: 23640495; PubMed Central PMCID: PMCPMC3954496.
Krams R, et al: Evaluation of Endothelial Shear Stress and 3D Geometry as Factors Determining the Development of Atherosclerosis and Remodeling in Human Coronary Arteries in Vivo: Combining 3D Reconstruction from Angiography and IVUS (ANGUS) with Computational Fluid Dynamics. Arteriosclerosis, Thrombosis, and Vascular Biology 1997, 17 (10):2061-2065.
Ku ON, et al. Pulsatile flow and atherosclerosis in the human carotid bifurcation. Positive correlation between plaque location and low oscillating shear stress. Arteriosclerosis. 1985;5(3):293-302. PubMed PMID: 3994585.
Kubo T, et al. The dynamic nature of coronary artery lesion morphology assessed by serial virtual histology intravascular ultrasound tissue characterization. J Am Coll Cardiol. 2010;55(15):1590-7. PubMed PMID: 20378076.
Lau B, et al: Imaging true 3D endoscopic anatomy by incorporating magnetic tracking with optical coherence tomography: proof-of-principle for airways. Opt Express 2010, 18(26):27173-27180.
Li BH, et al. Hybrid intravascular ultrasound and optical coherence tomography catheter for imaging of coronary atherosclerosis. Catheterization and cardiovascular interventions : official journal of the Society for Cardiac Angiography & Interventions. 2013;81 (3):494-507. PubMed PMID: 22566368.
Li J, et al. Miniature optical coherence tomography-ultrasound probe for automatically coregistered three-dimensional intracoronary imaging with realtime display. J Biomed Opt. 2013; 18(10):100502. PubMed PMID: 24145701; PubMed Central PMCID: PMCPMC3801153.
Liu H, et al. Large-scale single-chirality separation of single-wall carbon nanotubes by simple gel chromatography. Nat Commun. 2011 ;2:309. PubMed PMID: 21556063; PubMed Central PMCID: PMCPMC3113293.
Liu L, et al. Imaging the subcellular structure of human coronary atherosclerosis using micro-optical coherence tomography. Nat Med. 2011 ; 17(8):1010-4. PubMed PMID: 21743452; PubMed Central PMCID: PMCPMC3151347.
Malek AM, et al. Hemodynamic shear stress and its role in atherosclerosis. JAMA. 1999;282(21 ):2035-42. PubMed PMID: 10591386.
Mandal K, et al. Vessel-based registration of an optical shape sensing catheter for MR navigation. Int J Comput Assist Radial Surg. 2016; 11(6):1025-34. PubMed PMID: 26984556.
Manfrini O, et al. Sources of error and interpretation of plaque morphology by optical coherence tomography. Am J Cardiol. 2006;98(2):156-9. PubMed PMID: 16828584.
Masdjedi K, et al. Navvus FFR to reduce CONTRAst, Cost and radiation (CONTRACT); insights from a single-centre clinical and economical evaluation with the RXi Rapid-Exchange FFR device. Int J Cardiol. 2017. PubMed PMID: 28161129.
Mastey V, et al. Cost-effectiveness of PCSK9 Inhibitor Therapy. JAMA. 2016;316(20):2151-2. PubMed PMID: 27893122.
Minami Y, et al. Clinical utility of quantitative bright spots analysis in patients with acute coronary syndrome: an optical coherence tomography study. Int J Cardiovasc Imaging. 2015;31(8):1479-87. PubMed PMID: 26202158.
Moore JP, et al. Shape sensing using multi-core fiber optic cable and parametric curve solutions. Opt Express. 2012;20(3):2967-73.
Nikolic B, et al. Strain- and torsion-induced resonance energy tuning of Raman scattering in single-wall carbon nanotubes. physica status solidi (b ). 2016;253(12):2391-5.

(56) References Cited

OTHER PUBLICATIONS

Oemrawsingh PV, et al., "Intravascular ultrasound guidance improves angiographic and clinical outcome of stent implantation for long coronary artery stenoses: final results of a randomized comparison with angiographic guidance (TULIP Study)." Circulation 107.1 (2003): 62-67.
Oemrawsingh RM, et al. Near-infrared spectroscopy predicts cardiovascular outcome in patients with coronary artery disease. J Am Coll Cardiel. 2014;64(23):2510-8. PubMed PMID: 25500237.
Otsuka F, et al. The importance of the endothelium in atherothrombosis and coronary stenting. Nat Rev Cardiel. 2012;9(8):439-53. PubMed PMID: 22614618.
Papafaklis MI, et al. Incremental predictive value of combined endothelial shear stress, plaque necrotic core, and plaque burden for future cardiac events: A post-hoc analysis of the PREDICTION study. Int J Cardiol. 2016;202:64-6. PubMed PMID: 26386924.
Papafaklis MI, et al. "Anatomically correct three-dimensional coronary artery reconstruction using frequency domain optical coherence tomographic and angiographic data: head-to-head comparison with intravascular ultrasound for endothelial shear stress assessment in humans." EuroIntervention 11.4 (2015): 407-415.
Parise H, et al. Meta-analysis of randomized studies comparing intravascular ultrasound versus angiographic guidance of percutaneous coronary intervention in pre-drugeluting stent era. Am J Cardiel. 2011;107(3):374-82. PubMed PMID: 21257001.
Pasterkamp G, et al. Temporal shifts in clinical presentation and underlying mechanisms of atherosclerotic disease. Nat Rev Cardiol. 2017; 14(1 ):21-9. PubMed PMID: 27762311.
Pedrigi RM, et al. Inducing Persistent Flow Disturbances Accelerates Atherogenesis and Promotes Thin Cap Fibroatheroma Development in D374Y-PCSK9 Hypercholesterolemic Minipigs. Circulation. 2015; 132(11):1003-12. PubMed PMID: 26179404.
Phipps JE, et al. Diagnosis of Thin-Capped Fibroatheromas in Intravascular Optical Coherence Tomography Images: Effects of Light Scattering. Circ Cardiovasc Interv. 2016;9(7). PubMed PMID: 27406987; PubMed Central PMCID: PMCPMC4946571.
Quillard T, et al. TLR2 and neutrophils potentiate endothelial stress, apoptosis and detachment: implications for superficial erosion. Eur Heart J. 2015;36(22):1394-404. PubMed PMID: 25755115; PubMed Central PMCID: PMCPMC4458287.
Samady H, et al. Coronary artery wall shear stress is associated with progression and transformation of atherosclerotic plaque and arterial remodeling in patients with coronary artery disease. Circulation. 2011;124 (7):779-88. PubMed PMID: 21788584.
Slager CJ, et al: True 3-Dimensional Reconstruction of Coronary Arteries in Patients by Fusion of Angiography and IVUS (ANGUS) and Its Quantitative Validation. Circulation 2000, 102(5):511-516.
Stone GW, et al. A prospective naturalhistory study of coronary atherosclerosis. N Engl J Med. 2011;364(3):226-35. PubMed PMID: 21247313.
Stone P, et al. "Role of low endothelial shear stress and plaque characteristics in the prediction of nonculprit major adverse cardiac events: the PROSPECT Study." JACC: Cardiovascular Imaging 11.3 (2018): 462-471.
Stone P, et al. Local low endothelial shear stress provides incremental prediction of non-culprit major adverse cardiac events beyond plaque burden, minimal lumen area, and morphology: The PROSPECT Study. In: Circulation, editor. American Heart Association Annual Meeting; Orange County, CA. 2015.
Stone PH, et al. Effect of endothelial shear stress on the progression of coronary artery disease, vascular remodeling, and in-stent restenosis in humans: in vivo 6-month follow-up study. Circulation. 2003; 108(4 ):438-44. Pub Med PMID: 12860915.
Stone PH, et al. Prediction of progression of coronary artery disease and clinical outcomes using vascular profiling of endothelial shear stress and arterial plaque characteristics: the PREDICTION Study. Circulation. 2012; 126(2): 172-81. PubMed PMID: 22723305.
Strano MS, et al. Electronic structure control of single-walled carbon nanotube functionalization. Science. 2003;301 (5639):1519-22.
Sun P, et al. Carbon nanotubes as non-contact optical strain sensors in smart skins. The Journal of Strain Analysis for Engineering Design. 2015;50(7):505 12.
Tarantini G, et al. Left Anterior Descending Artery Myocardial Bridging: A Clinical Approach. J Am Coll Cardiel. 2016;68(25):2887-99. PubMed PMID: 28007148.
Tearney GJ, et al. Quantification of macrophage content in atherosclerotic plaques by optical coherence tomography. Circulation. 2003;107(1):113-9. PubMed PMID: 12515752.
Thondapu V, et al. Biomechanical stress in coronary atherosclerosis: emerging insights from computational modelling. Eur Heart J. 2016. PubMed PMID: 26903533.
Tonino PA, et al. Angiographic versus functional severity of coronary artery stenoses in the FAME study fractional flow reserve versus angiography in multivessel evaluation. J Am Coll Cardiel. 2010;55(25):2816-21. PubMed PMID: 20579537.
Tonino PA, et al. Fractional flow reserve versus angiography for guiding percutaneous coronary intervention. N Engl J Med. 2009;360(3):213-24. PubMed PMID: 19144937.
Toutouzas K, et al. Accurate and reproducible reconstruction of coronary arteries and endothelial shear stress calculation using 30 OCT: comparative study to 30 IVUS and 30 QCA. Atherosclerosis. 2015;240(2):510-9. PubMed PMID: 25932791.
Ughi GJ, et al. Automated segmentation and characterization of esophageal wall in vivo by tethered capsule optical coherence tomography endomicroscopy. Biomed Opt Express. 2016;7(2):409-19. PubMed PMID: 26977350; PubMed Central PMCID: PMCPMC4771459.
Ughi GJ, et al. Clinical Characterization of Coronary Atherosclerosis With Dual Modality OCT and Near-Infrared Autofluorescence Imaging. JACC Cardiovasc Imaging. 2016;9(11 ):1304-14. PubMed PMID: 26971006; PubMed Central PMCID: PMCPMC5010789.
Ulissi ZW, et al. 2D equation-of-state model for corona phase molecular recognition on single-walled carbon nanotube and graphene surfaces. Langmuir. 2015;31 (1 ):628-36. PubMed PMID: 25470315.
Wald OS, et al. Randomized trial of preventive angioplasty in myocardial infarction. N Engl J Med. 2013;369 (12):1115-23. PubMed PMID: 23991625.
Walsh JH, et al: Evaluation of pharyngeal shape and size using anatomical optical coherence tomography in individuals with and without obstructive sleep apnoea. Journal of Sleep Research 2008, 17(2):230-238.
Wang T, et al. Heartbeat OCT and Motion-Free 3D In Vivo Coronary Artery Microscopy. JACC Cardiovasc Imaging. 2016;9(5):622-3. PubMed PMID: 27151524.
Wang Y, et al. GPU accelerated real-time multifunctional spectral-domain optical coherence tomography system at 1300 nm. Opt Express. 2012;20(14):14797-813. PubMed PMID: 22772175; PubMed Central PMCID: PMCPMC3443681.
Wischgoll T, et al. Validation of image-based method for extraction of coronary morphometry. Ann Biomed Eng. 2008;36(3):356-68. PubMed PMID: 18228141.
Withey PA, et al. Strain paint: noncontact strain measurement using single-walled carbon nanotube composite coatings. Nano Lett. 2012;12(7):3497-500. PubMed PMID: 22694748.
Wojtkowski M, et al. Ultrahigh resolution, highspeed, Fourier domain optical coherence tomography and methods for dispersion compensation. Optics Express. 2004; 12(11 ):2404-22.
Yoo H, et al. Intra-arterial catheter for simultaneous microstructural and molecular imaging in vivo. Nat Med. 2011; 17 (12):1680-4. PubMed PMID: 22057345; PubMed Central PMCID: PMCPMC3233646.
Zarins CK, et al. Carotid bifurcation atherosclerosis. Quantitative correlation of plaque localization with flow velocity profiles and wall shear stress. Circ Res. 1983;53(4 ):502-14. PubMed PMID: 6627609.
Zhang J, et al. Polarization-maintaining buffered Fourier domain mode locked swept source for optical coherence tomography. Optics letters. 2011; 36(24 ):4788-90. PubMed PMID: 22179884; PubMed Central PMCID: PMC3337216.
Cheng JM, et al. In vivo detection of high-risk coronary plaques by radiofrequency intravascular ultrasound and cardiovascular outcome: results of the ATHEROREMO-IVUS study. Eur Heart J.

(56) References Cited

OTHER PUBLICATIONS

2014;35(10):639-47. PubMed PMID: 24255128.

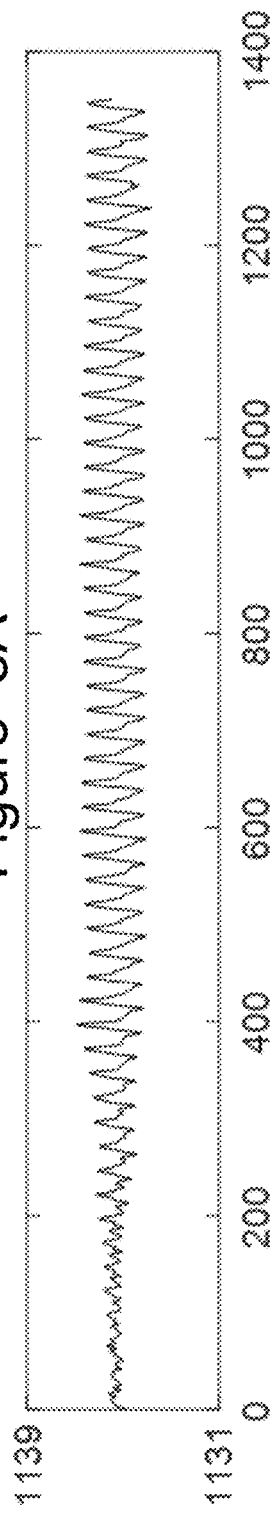
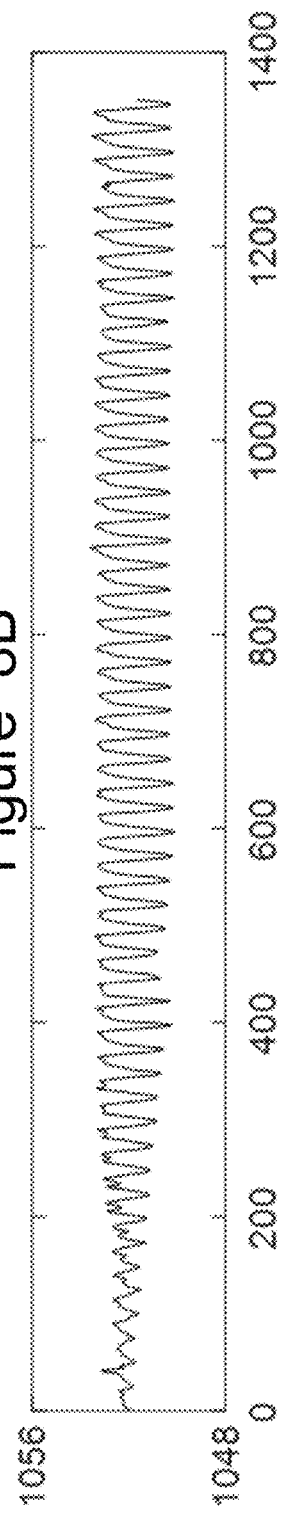
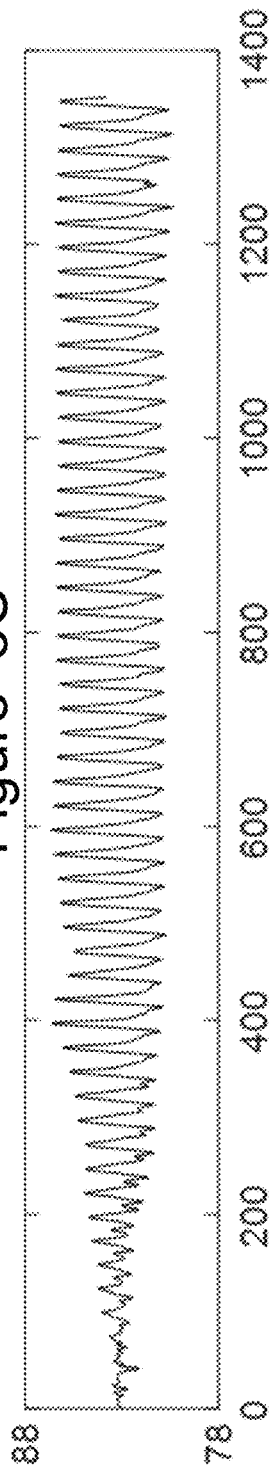

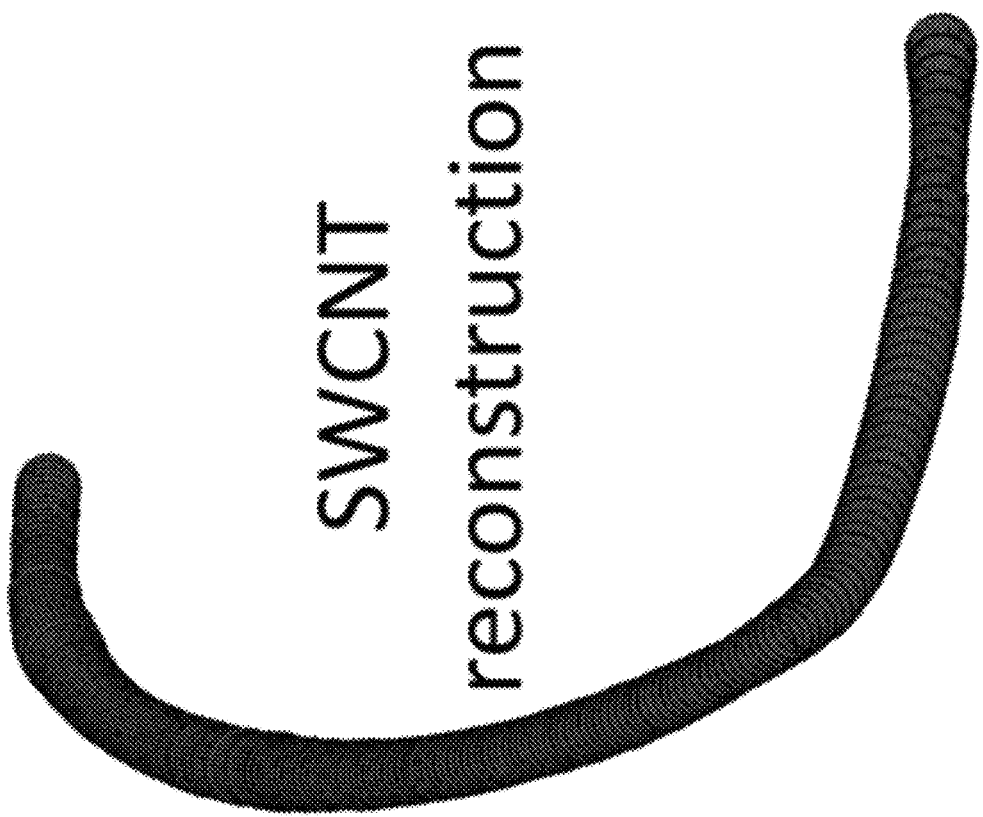
Figure 13A  3D-Model
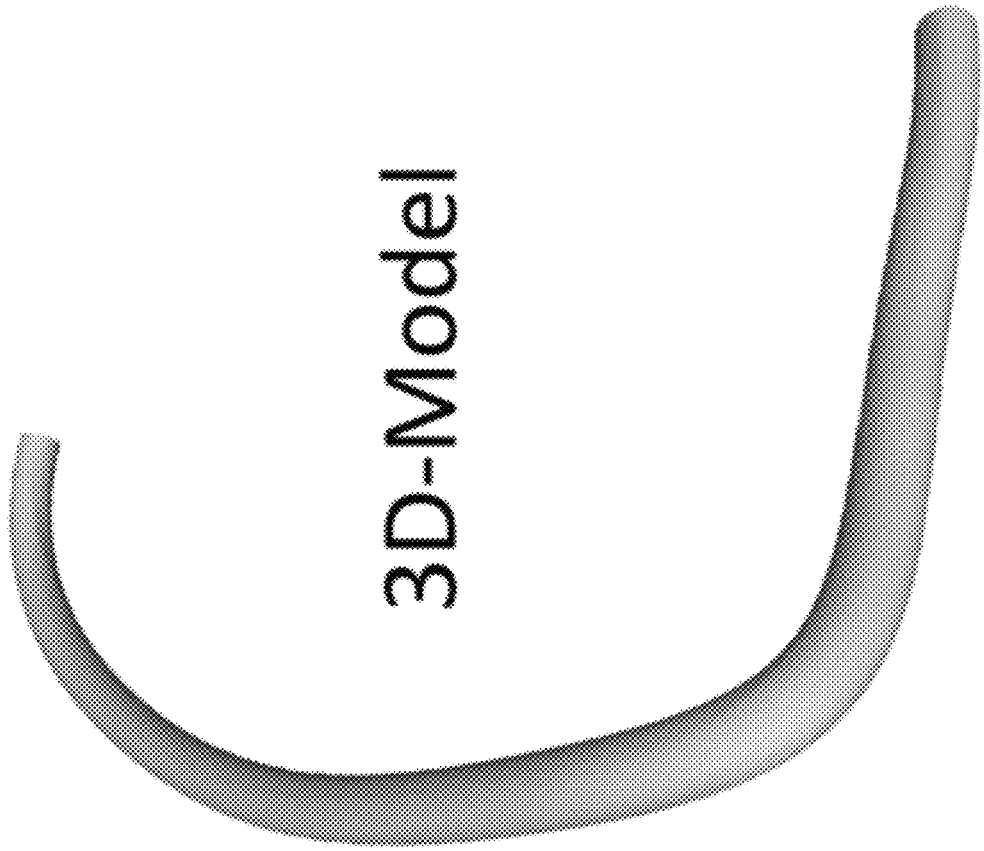
Figure 13B  SWCNT reconstruction

APPARATUS, METHODS AND COMPUTER-ACCESSIBLE MEDIA FOR IN SITU THREE-DIMENSIONAL RECONSTRUCTION OF LUMINAL STRUCTURES

CROSS-REFERENCE TO RELATED APPLICATIONS

This application is a continuation of U.S. application Ser. No. 17/849,072 filed on Jun. 24, 2022, which is a continuation of U.S. application Ser. No. 16/496,204 filed on Sep. 20, 2019, and issued as U.S. Pat. No. 11,406,318 on Aug. 9, 2022, and which represents the U.S. National Stage of PCT Application No. PCT/US2018/024014 filed on Mar. 23, 2018, which claims the benefit of U.S. Provisional Patent Application Ser. No. 62/475,304 filed on Mar. 23, 2017, and entitled "Apparatus, Methods and Computer-Accessible Media for in Situ Three-Dimensional Reconstruction of a Luminal Structure," which is incorporated by reference herein in its entirety.

FIELD OF THE DISCLOSURE

The present disclosure relates to three-dimensional imaging and reconstruction, and more particularly to exemplary embodiments of apparatus, method, and computer-accessible media for imaging of cylindrical structures, and even more particularly, e.g., for imaging luminal structures in the human body such as the vascular system and gastrointestinal tract.

BACKGROUND INFORMATION

True three-dimensional (3D) reconstruction is a desirable feature for several applications such as measurement of endothelial sheer stress (ESS) to diagnose progression of coronary artery disease and to diagnose sleep apnea in the airway lumen. 3D anatomical structures of the airways have been successfully reconstructed with the use of magnetic sensors. However, the large size of magnetic sensor catheters has forced cardiologists to rely on biplane angiography images to reconstruct the 3D shape of the coronary artery. Intravascular ultrasound (IVUS) imaging and biplane angiography have been applied in some studies to calculate ESS; however, the repeated use of angiography is often not desirable because of complications such as the ionization capability of X-rays used in this process. Additionally, ESS measurements are obtained through a labor-intensive and time-consuming post-processing procedure, making it unsuitable for on-line applications. Another approach to determining the 3D shape of an artery proposes to use a shape-sensing catheter that employs optical frequency domain reflectometry (OFDR) with either multiple fibers or a single fiber with multiple cores that contains distributed fiber Bragg gratings. This technique requires additional optical fibers that would increase the diameter of the catheter and make the rotary junction and imaging system more complicated.

There is a need to find alternative minimal invasive technologies having high resolution imaging and 3D reconstruction capabilities.

SUMMARY OF THE INVENTION

Optical coherence tomography (OCT) has emerged as a new imaging modality which provides images similar to IVUS but with much higher resolution. When applied to luminal structures, OCT obtains high resolution images of the surface and underlying structures of the lumen. However, OCT does not provide the overall three-dimensional shape of the lumen and therefore another methodology is desired which can provide information to accurately reconstruct the 3D shape while providing high-resolution OCT images of the lumen and microstructure. Recently, carbon nanotube-based composite coatings have been used to measure strain in materials. Accordingly, this technique may be applied to the measurement of 3D shape by measuring local strain-induced spectroscopic information from a carbon-nanotube based strain sensor, which is related to the curvature of the sheath that is typically used to house an OCT catheter during intraluminal imaging. Such a strain-sensitive OCT that measures its own shape is employed in various embodiments disclosed herein in order to circumvent the time-consuming process of registering the angiogram with intravascular imaging data.

In this invention, a dual channel (e.g. OCT plus strain measurement) system is demonstrated which is capable of measuring the 3D luminal shape while acquiring high resolution cross-sectional images. This method is not limited to coronary arteries and may be applied to obtain the 3D shape of any luminal or tubular structure, such as other blood or lymphatic vessels, or intraluminal organ including but not limited to the esophagus, ducts, intestines, ureter, pulmonary airways, pharynx, or a non-biological tubular structures such as a pipe, conduit, tunnel, etc. Furthermore, structural information may be obtained by other imaging modalities besides OCT (e.g. various embodiments of OCT such as polarization-sensitive OCT, 1-micron high-resolution OCT, ultrasound, intravascular ultrasound (IVUS) and photoacoustic ultrasound) such as stereo imaging, shape from motion or blurring, computed tomography, x-ray imaging, projection tomography, magnetic resonance imaging, etc. The system and concepts of this work are disclosed herein.

Thus, in one aspect the invention provides for an apparatus including at least one optical waveguide that emits electromagnetic radiation, a scanning arrangement that at least one of rotates and translates to direct the electromagnetic radiation, a strain-sensing sheath that at least partially encloses the at least one optical waveguide and the scanning arrangement, the strain-sensing sheath including a strain-sensing system optically coupled to the at least one waveguide; and a controller coupled to the strain-sensing system. The controller, using the strain-sensing system, is to: determine a first strain of the strain-sensing sheath at a first location, and determine a second strain of the strain-sensing sheath at a second location, the first location being different from the second location. The controller is further to: determine a curvature of the sheath between the first location and the second location based on determining the first strain and the second strain of the strain-sensing sheath.

In another aspect the invention provides for an apparatus which includes a catheter including a lens, a strain-sensing system, and a controller. The catheter is disposed within a strain-sensing sheath such that the lens rotates and translates within the strain-sensing sheath. The strain-sensing system is optically coupled to the catheter. The controller is coupled to the strain-sensing system. The controller, using the strain-sensing system, is to: determine a first strain of the strain-sensing sheath at a first location, and determine a second strain of the strain-sensing sheath at a second location, the first location being different from the second location. The controller is further to: determine a catheter curvature of the catheter between the first location and the second location based on determining the first strain and the second strain of the strain-sensing sheath.

In yet another aspect, the invention provides for a method which includes: providing a catheter having optically coupled thereto a strain-sensing system, the catheter including a lens, the catheter disposed within a strain-sensing sheath such that the lens rotates and translates within the strain-sensing sheath; determining, by a controller in communication with the strain-sensing system, a first strain of the strain-sensing sheath in an x-z plane and a y-z plane at a first location within the strain-sensing sheath; determining, by the controller, a second strain of the strain-sensing sheath in an x-z plane and a y-z plane at a second location within the strain-sensing sheath, the first location being different from the second location; and determining, by the controller, a catheter curvature between the first location and the second location based on determining the first strain and the second strain of the strain-sensing sheath.

In still another aspect, the invention provides for an apparatus for determining a shape of a luminal sample. The apparatus includes a catheter including a lens, the catheter disposed within a strain-sensing sheath such that the lens rotates and translates within the strain-sensing sheath; a structural imaging system optically coupled to the catheter; a strain-sensing system optically coupled to the catheter; and a controller coupled to the strain-sensing system and the structural imaging system. The controller, using the structural imaging system, is to: determine a first position of the catheter relative to the luminal sample at a first location within the strain-sensing sheath, and determine a second position of the catheter relative to the luminal sample at a second location within the strain-sensing sheath, the first location being different from the second location. The controller, using the strain-sensing system, is to: determine a first strain of the strain-sensing sheath at the first location, and determine a second strain of the strain-sensing sheath at the second location, and the controller further to: determine a first local curvature of the luminal sample relative to the catheter between the first location and the second location based on determining the first position and the second position of the catheter relative to the luminal sample, determine a second local curvature of the catheter between the first location and the second location based on determining the first strain and the second strain of the strain-sensing sheath, and determine a third local curvature of the luminal sample between the first location and the second location based on determining the first local curvature and the second local curvature.

In yet another aspect, the invention provides for a method for determining a shape of a luminal sample. The method includes: providing a catheter having optically coupled thereto a structural imaging system and a strain-sensing system, the catheter including a lens, the catheter disposed within a strain-sensing sheath such that the lens rotates and translates within the strain-sensing sheath; determining, by a controller coupled to the strain-sensing system and the structural imaging system, a first position of the catheter relative to the luminal sample at a first location within the strain-sensing sheath; determining, by the controller, a second position of the catheter relative to the luminal sample at a second location within the strain-sensing sheath, the first location being different from the second location; determining, by the controller, a first strain of the strain-sensing sheath at the first location; determining, by the controller, a second strain of the strain-sensing sheath at the second location; determining, by the controller, a first local curvature of the luminal sample relative to the catheter between the first location and the second location based on determining the first position and the second position of the catheter; determining, by the controller, a second local curvature of the catheter between the first location and the second location based on determining the first strain and the second strain of the strain-sensing sheath; and determining, by the controller, a third local curvature of the luminal sample between the first location and the second location based on determining the first local curvature and the second local curvature.

The foregoing and other aspects and advantages of the invention will appear from the following description. In the description, reference is made to the accompanying drawings which form a part hereof, and in which there is shown by way of illustration preferred embodiments of the invention. Such embodiments do not necessarily represent the full scope of the invention, however, and reference is made therefore to the claims herein for interpreting the scope of the invention.

BRIEF DESCRIPTION OF THE DRAWINGS

Further objects, features and advantages of the present disclosure will become apparent from the following detailed description taken in conjunction with the accompanying figures showing illustrative embodiments of the present disclosure, in which:

FIG. 2B describes the strain-sensing molecules attached to the interior sheath wall; FIG. 2C describes strain-sensing molecules embedded within the sheath wall; and FIG. 2D shows an optical strain-sensing probe with a guidewire provision;

FIGS. 8A-8C show a series of graphs of peak frequency vs. frame number as a function of pullback position and rotation angle;

FIG. 13A shows 3D geometry of a human right coronary artery lumen that was 3D printed to create a physical phantom; FIG. 13B shows a 3D image of the phantom reconstructed by the SWCNT catheter.

DETAILED DESCRIPTION OF EXEMPLARY EMBODIMENTS

Figure 1:
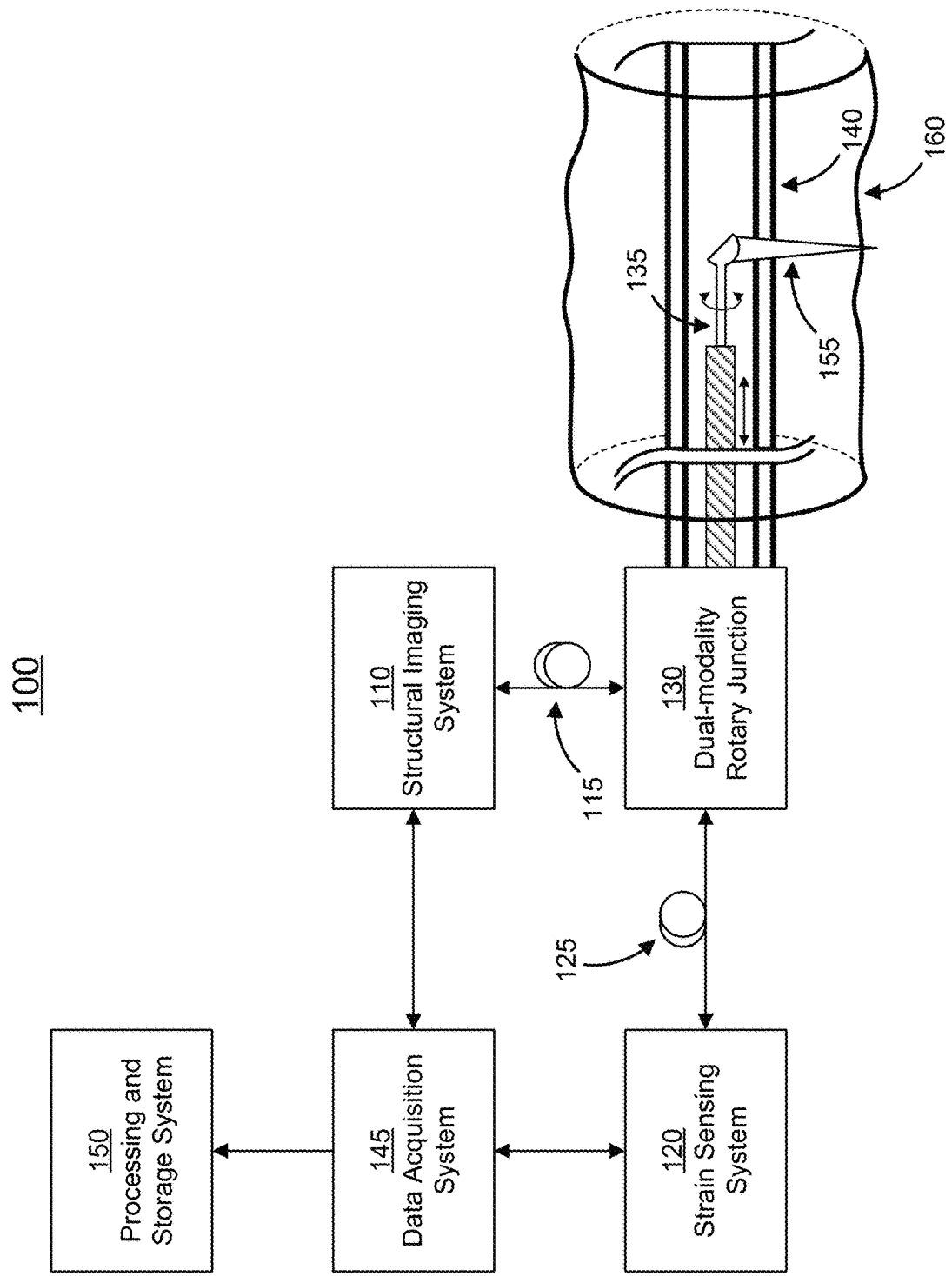
FIG. 1 is a schematic block diagram of an exemplary embodiment of the apparatus used to reconstruct the 3D shape of a luminal structure.

Thus, disclosed herein is the development of apparatus and methods, including embodiments of instrumentation, probes, and algorithms, to measure the three-dimensional shape of a luminal structure, including in vivo. The exemplary embodiments disclosed herein are applied to intracoronary imaging and can provide an input to computational models that estimate the endothelial shear stress on the artery wall. Nevertheless, the techniques and apparatus disclosed herein may be used to determine information about other luminal structures in addition to coronary vessels.

A particular feature of the present disclosure is that a three-dimensional shape of a luminal structure such as a coronary artery can be reconstructed using structural data acquired from a structural imaging system, such as optical coherence tomography, and from a strain-sensing system based upon, for example fluorescence emission of single-walled carbon nanotubes affixed to a sheath. The present disclosure may be embodied in clinical instruments, intra-coronary catheters, and methods that may be used to reconstruct the 3D shape of a coronary artery (or other luminal structure) in real-time and further that this input may be used to provide real-time 3D coronary shapes for computational fluid dynamics models that estimate endothelial shear stress (ESS) in patients undergoing percutaneous coronary interventions.

Diagnosis and treatment of coronary artery disease (CAD) is hindered by an inability to investigate fundamental pathobiological processes that lead to coronary atherosclerotic plaque progression and destabilization in humans. A critical mechanism responsible for plaque behavior is local shear stress experienced by endothelial cells, governed by the geometry of the vessel and, consequently, the local patterns of blood flow. In regions of low ESS, endothelial cells respond by increasing permeability to protein complexes such as LDL and further trigger a variety of proatherogenic, proinflammatory, and prothrombotic processes at that site. This low shear stress milieu is the environment that uniquely dictates a pathobiological endothelial response and atherosclerotic plaque progression/destabilization.

Recently, methods have been developed for computing ESS of human coronary arteries in vivo. Reconstruction of the 3D anatomy of each coronary artery is accomplished by registering intracoronary optical coherence tomography (OCT) or intravascular ultrasound (IVUS) imaging data to specially-acquired angiograms. This 3D anatomic data is then input into a computational fluid dynamics (CFD) model that computes ESS at the coronary artery's luminal surface. These techniques have now been used in natural history clinical studies; results show that low ESS is the most powerful predictor of future coronary events. However, ESS measurements cannot currently be obtained in the cardiac catheterization lab in real-time, as registration of imaging data, 3D reconstruction, and CFD modeling are time-consuming and must be performed off-line. Due of these limitations, it takes hours to compute the ESS maps for each artery in any given patient.

Thus, the methods and apparatus of the present disclosure may help to improve outcomes of patients by enabling real-time ESS (RT-ESS) measurement during routine cardiac catheterization to guide personalized management of CAD. The simplicity, efficiency, and precision delivered by the proposed RT-ESS technology provides a significant improvement in the ability to use ESS information in research and clinical practice.

Accordingly, the present disclosure describes the development of RT-ESS technology for clinical CAD patient management. A shape-sensing OCT-NIRF (near-infrared fluorescence) imaging catheter and automated image processing algorithms can accurately and rapidly reconstruct the coronary artery without requiring an angiogram. In various embodiments, the inner surface of the RT-ESS catheter's sheath may be coated with single-walled carbon nanotubes (SWCNTs), which have strain-dependent NIR fluorescence spectra. Fluorescence spectra from the sheath can be acquired and analyzed as the catheter's optics are helically scanned, providing the shape (centerline) of the catheter. OCT images of the artery wall, acquired simultaneously with the fluorescence spectra, may be automatically segmented and mapped to the catheter's centerline to provide a true 3D representation of the artery's lumen.

In various embodiments, the 3D arterial geometry can be used to generate a 3D mesh for CFD modeling. Using patient-specific blood viscosity and artery-specific blood flow rates, flow simulations can be performed in the mesh via a highly parallel CPU workstation running a pressure-based coupled parallel solver.

A schematic block diagram of an exemplary embodiment of a 3D-shape sensing device with shape sensing probe according to the present disclosure is shown in FIG. 1. This exemplary device apparatus can include a structural imaging system 110, which generates images of a luminal object's 160 microstructure, a strain-sensing system 120, which generates data from which the 3D shape of a luminal object 160 can be reconstructed, output of the structural imaging system 115, output of the strain-sensing system 125, a dual modality rotary junction unit 130, a strain-sensing probe 135 with a sheath 140, a data acquisition system 145, and data processing and storage unit 150. It should be understood that a plurality of each of these described systems, arrangements and elements can be included and/or implemented in or together with the exemplary apparatus.

The structural imaging system 110 is designed to collect back-reflected signals that can be either optical or mechanical in nature from a luminal structure 160 to acquire information regarding the luminal surface and underlying microstructure. The exemplary structure is tissue and in particular a coronary artery. Depth-resolved microstructural images obtained from the structural imaging system 110 can contain features related to the probe sheath 140 as well as the luminal surface and subsurface.

In the exemplary embodiment, the structural imaging system 110 will implement optical coherence tomography (OCT) or other OCT-related modalities to produce depth-resolved microstructural images. Other OCT-related modalities include optical frequency domain imaging (OFDI), polarization-sensitive optical coherence tomography (ps-OCT), and other embodiments of higher-resolution OCT, also known as μOCT, that can employ a distal optical design to extend the depth of focus while maintaining a sub 10-μm lateral spot size.

In another embodiment, the structural imaging system may implement intravascular ultrasound (IVUS) or photoacoustic ultrasound imaging to investigate the tissue microstructure. Similar to OCT, both technologies produce transverse images that are automatically registered to strain measurements.

The strain-sensing system 120 contains instrumentation and components that can enable either fluorescence spectroscopy, Raman spectroscopy, or absorption spectroscopy. Localized material strain is encoded in the central wavelength of the molecular spectrum. Although instrumentation is specific to the spectroscopic technique used, in general each spectroscopic technology requires a light source for probing the molecular signature, a dispersing element such as a prism, grating, spectrometer, or spectrograph to separate the returned spectroscopic signal, and an optical detector to record the molecular signal. In an alternative embodiment, the source wavelength may be scanned as a function of time and similar information may be obtained by detecting the light spectroscopically without requiring a dispersive element in the detection path.

While the structural imaging system 110 can be connected to the dual modality rotary junction 130 via a single mode fiber 115, the strain-sensing system 120 can be connected with either a double-clad fiber (DCF) 125 or a combination of single-mode and/or multimode fibers. The dual modality rotary junction 130 can combine two optical beams from different modalities and serve as an interface between a stationary imaging platform and a helical scanning (rotation and translation) probe 135. Optical beam combining and splitting in the dual-modality rotary junction can be accomplished through the use of dichroic mirrors, beam splitters, or arrangement of dispersive elements. A transparent strain-sensing sheath 140 may be used to protect the probe 135 and may contain molecular strain-sensors that report the local curvature of the strain-sensing sheath 140 during a helical scan of the luminal structure. Optical beams 155 from the structural imaging 110 and strain-sensing 120 modalities can be delivered by a double-clad fiber within the probe 135 and interrogate the sheath and microstructure of a lumen, such as a coronary artery. An advantage of the DCF-based, mechanically-scanning OCT-fluorescence catheter is that the double clad fiber in the probe may be used to simultaneously collect co-localized and intrinsically co-registered OCT from the lumen and fluorescence light from the probe's sheath at each scan point. Light reflected from the luminal wall and fluorescence emission from the sheath is collected by the optical probe and transmitted to the dual modality rotary junction, where the back-reflected structural (e.g. OCT) light is separated and returned to the structural imaging system 110 and the spectroscopic signal (i.e. from the strain-sensing sheath 140) is returned to the strain-sensing system 120 for spectral analysis and detection. The resulting structural (e.g. OCT) and spectroscopic data is recorded by a data acquisition system 145 and these signals are analyzed and processed to reconstruct the three-dimensional shape of the luminal structure by a data processing and storage unit 150.

Figure 2A:
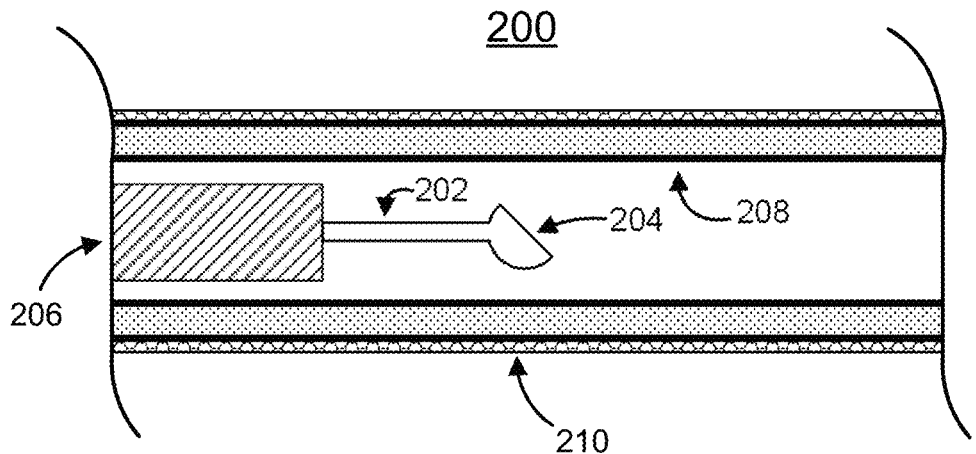
FIGS. 2A-2D are schematics of exemplary embodiments of optical strain-sensing probes employing a single sheath, where FIG. 2A describes the strain-sensing molecules attached to the exterior sheath wall.

Exemplary schematics of several strain-sensing sheaths designed for a side-viewing multimodality optical probe are presented in FIGS. 2A-2D. FIG. 2A describes an embodiment of a strain-sensing sheath 200 in which the strain-sensing molecules can be located on the exterior sheath wall. The dual modality optical probe includes an optical fiber 202 that transceives broadband light from the structural imaging system 110 and excitation light from the strain-sensing system 120. The distal end of the optical fiber is terminated with optics 204 that focus and collect the OCT and spectroscopic signals. The preferred optical fiber 202 used in the present embodiment is a double-clad fiber (DCF). The structure of a double-clad fiber incorporates a central core surrounded by an inner and outer cladding. The core is designed to transceive single-mode light while the inner cladding collects light similar to a multimode fiber. Structural imaging light (e.g. OCT) is transceived by the single mode core while the excitation light can be focused into either the core or inner cladding of the DCF while the returned emission light is collected by the inner cladding. The double-clad fiber 202 is threaded through a torque-transmitting driveshaft 206 and this assembly is then threaded into a thin-walled flexible sheath 208 that will conform to the shape of the luminal structure. In the embodiment of FIG. 2A, molecular strain sensors 210 are applied to the exterior of the sheath 208, which is in direct contact with the luminal structure (e.g., tissue). The materials of the sheath 208 and exterior coating/strain sensors 210 are chosen to be optically transparent to the broadband OCT light and spectroscopic signals. In preferred spectroscopic embodiment (e.g. fluorescence), excitation light is focused by the distal optics 204 and excites the molecular strain sensors, which emit red-shifted light that is collected by the distal optics and guided by the optical fiber 202 to the rotary junction 130, which separates the optical signals and sends them to their respective structural optical 110 and strain-sensing 120 systems.

Figure 2B:
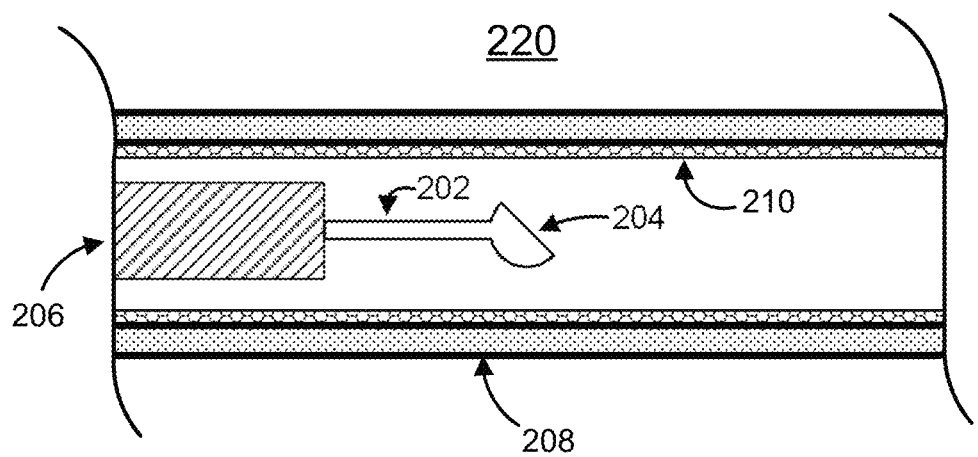
Figure 2C:
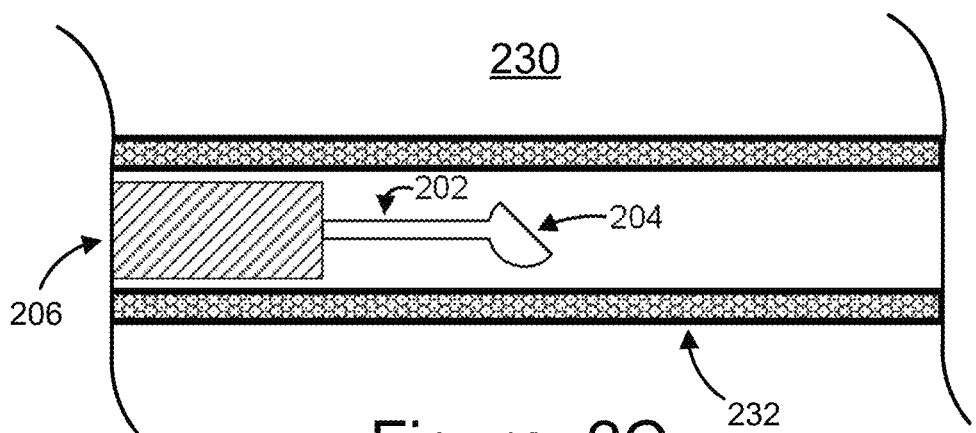
Figure 2D:
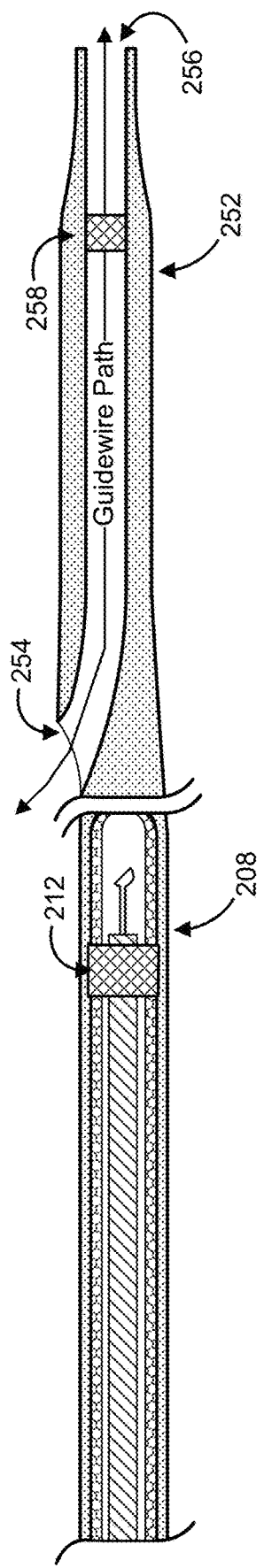

FIG. 2B presents an exemplary schematic of another embodiment of a strain-sensing optical probe 220 in which the molecular sensors 210 are applied to the interior wall of the sheath 208. This is a preferred embodiment since the molecular sensors are isolated from the luminal surface by sheath material thereby avoiding direct contact with the lumen (e.g. tissue and fluids). In the ideal case, the coating containing the molecular sensors is thin, to accommodate free, uniform rotation of the driveshaft. FIG. 2C presents another exemplary schematic of yet another embodiment of a strain-sensing optical probe 230 in which the molecular sensors are embedded in the sheath materials at the time of sheath extrusion. A second polymer that does not contain molecular sensors may be coextruded outside of the inner strain-sensing polymer to isolate the lumen (e.g. tissue and fluids) from direct exposure to the sensors. As shown in FIG. 2D, any of the disclosed embodiments (including those in FIGS. 2A-2C, 3, and 4A-4B) may include a guidewire provision 252 including a guidewire path (with openings 254 and 256 for entry and exit of a guidewire). In addition, the guidewire provision 252 may include a radiopaque tip marker 258 to help locate the probe 200 in a subject using for example fluoroscopy. Furthermore, each of the embodiments (including those in FIGS. 2A-2C, 3, and 4A-4B) may optionally include a radiopaque lens marker 212 as shown in FIG. 2D to help locate the probe 200 in a subject using for example fluoroscopy.

Figure 3:
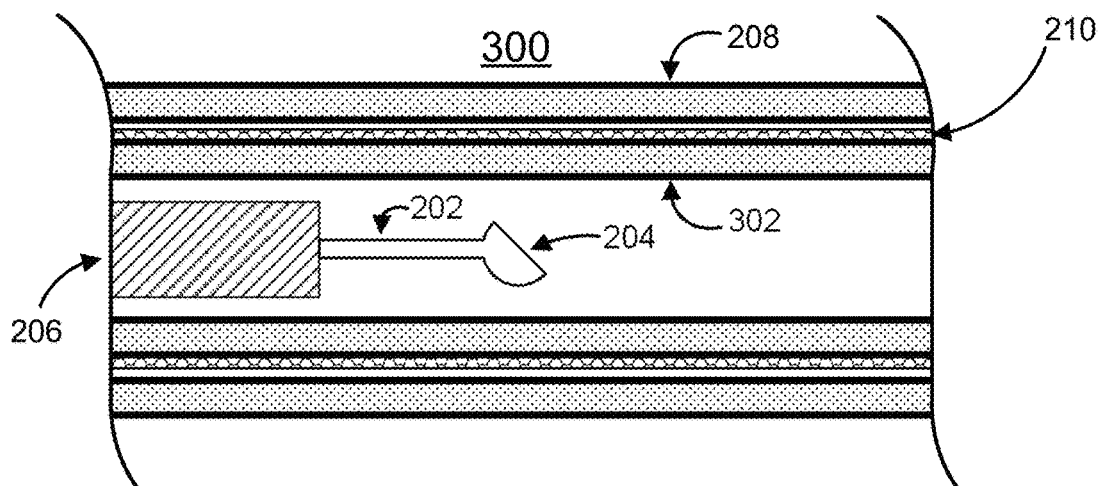
FIG. 3 is a schematic of a strain-sensing optical probe with the molecular strain sensors embedded on the exterior of the inner sheath that is inside of an outer sheath.

A second exemplary embodiment of strain-sensing optical probe 300 is presented in FIG. 3. In this embodiment, a second smaller diameter inner sheath 302 is coated with strain-sensing molecules 210 and can then be threaded inside of a larger exterior sheath 208. The optical fiber/driveshaft assembly is then threaded into the smaller diameter sheath 302. This embodiment has the advantage that it does not alter the properties of the exterior sheath 208.

Figure 4A:
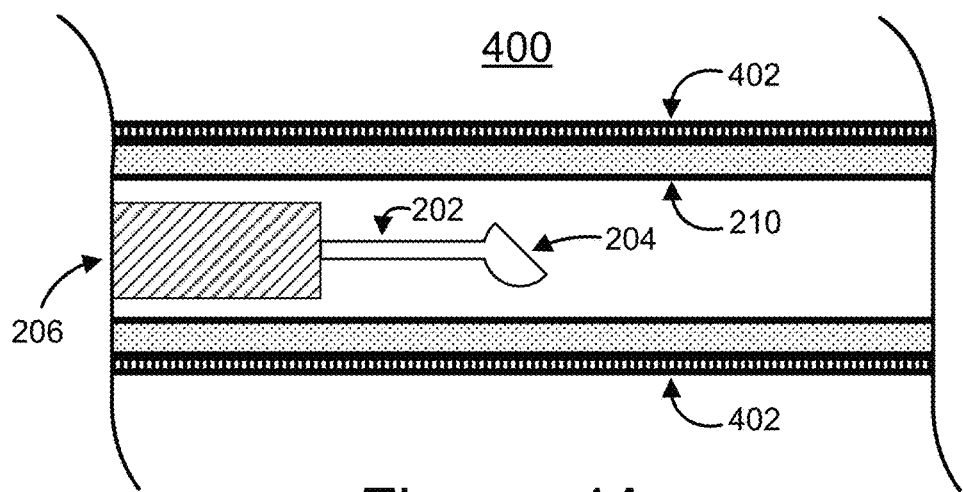
FIGS. 4A and 4B are schematics of a strain sensing optical probe where the molecular strain sensors are embedded as thin wires that are disposed on the exterior of the sheath.
Figure 4B:
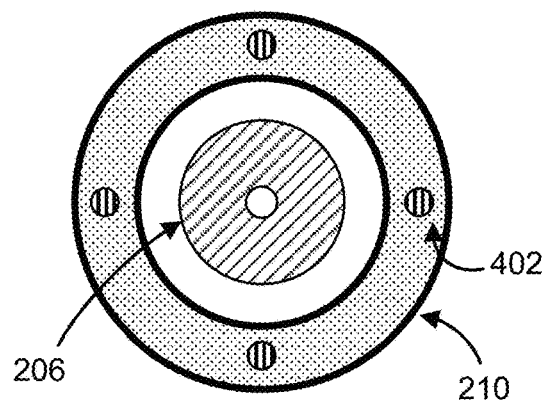

Accurate reconstruction of the 3D shape of a luminal structure depends upon the uniform rotation and pullback of driveshaft through the strain-sensing sheath. Non uniform rotational distortion (NURD) can negatively impact the 3D reconstruction. Corrections for NURD or torsion-induced fluorescence can be identified and corrected by adding a fiducial marker to the sheath that can be detected by both modalities. In a third exemplary embodiment of a strain-sensing sheath, strain sensing molecules can be incorporated in thin threads or wires 402 that are themselves embedded in the sheath, as presented in FIGS. 4A and 4B. FIG. 4A shows a cross-sectional side view and FIG. 4B shows a cross-sectional end view of the optical probe 400. In this particular embodiment, four sensing wires 402 are embedded within the sheath at 90° radial locations from each other. In the preferred embodiment, the wires coated with strain-sensing molecules can be embedded in the sheath 210 during the extrusion process. In another embodiment, the strain-sensing wires 402 can be attached to the exterior of the sheath 210 and sealed in place by a polymer over-sheath or a thin application of curable polymer materials. In various embodiments, fewer than four wires or greater than four wires may be used; generally the wires are equally spaced around the outer circumference of the sheath.

Molecular strain sensors are molecules or macromolecules whose electronic structure changes predictably in response to changes in the strain of the host material as it undergoes compression or stretching. An exemplary strain-sensing material is single-walled carbon nanotubes (SWCNTs). SWCNTs are a class of nanoscale tubes composed completely of covalently-bonded carbon atoms. Each SWCNT has a well-defined molecular structure characterized by a pair of integers (n,m) that specifies the tube diameter and roll-up angle of the SWCNT. The physical structure of a SWCNT controls its electronic structure, and thus the spectral transitions that the SWCNT undergoes. Axial stretching and compression of individual SWCNT results in predictable changes in the electronic structure, which systematically perturbs the molecular structure and shifts the spectral transition resulting in a frequency (wavelength) shift in the fluorescence, absorption, or Raman spectrum when the nanotube is strained. It has been established in the literature that the direction of the strain-induced spectral shift occurs in opposite directions for SWCNT of different modulus (n−m,3). For example, the peak emission wavelength shifts in the fluorescence spectra can be large enough to detect axial strains as low as 0.1% in some embodiments.

In an exemplary embodiment 200, a coating 210 containing SWCNT may be applied to the exterior of a coronary catheter sheath 208 as shown in FIG. 2A. The strain-sensing coating was prepared by dispersing single-walled nanotubes grown via the CoMoCAT process in a mixture of poly(9,9-di-n-octylfluorenyl-2,7-diyl) (PFO) and toluene. The solution was tip-sonicated at 1 W/ml for 30 minutes and followed by centrifugation for 30 minutes. The clear supernatant containing the isolated nanotubes was removed. As per the literature, the solubility of nanotubes is low in nearly all solvents. The strong non-covalent interactions between PFO and SWCNT resulted in single-wrapped nanotubes that isolate chiralities (7,5) and (7,6). After centrifugation, the clear solution containing enriched (7,5) and (7,6) nanotubes was mixed with a commercially-available oil-based polyurethane (Minwax FastDrying SemiGloss Polyurethane) at a ratio of 1:1. The exterior of a coronary catheter sheath 208 was dip-coated in the SWCNT-polymer solution and allowed to cure. Multiple layers may be deposited along the 10-cm-long distal segment to optimize the fluorescence signal. In this exemplary coating, the average coating thickness of 36 μm varied by only ±6 μm. Due to the thin coating, the catheter sheath maintained its flexibility to within 5% as assessed by a standard gravity-induced deflection test.

In another exemplary method to achieve high concentrations of individually dispersed (7,5) and (7,6) nanotubes, single-chirality separation and purification may be achieved by suspending the nanotubes in a aqueous solution of sodium dodecyl sulfate (SDS) and using ultrasound sonication. After sonication, SWCNT suspensions may be ultra-centrifuged to remove aggregates and the SWCNT solution may be subjected to multistage gel chromatography. With this method, the concentration of nanotubes in solution can be on the order of 1 μg/ml, which can be several orders of magnitude above that used for the examples disclosed herein. The enriched nanotube solution can be mixed with a curable polymer coating according to embodiments 200, 220, and 230 or mixed into a polymer feedstock prior to extrusion according to embodiments 300 and 400.

Figure 5:
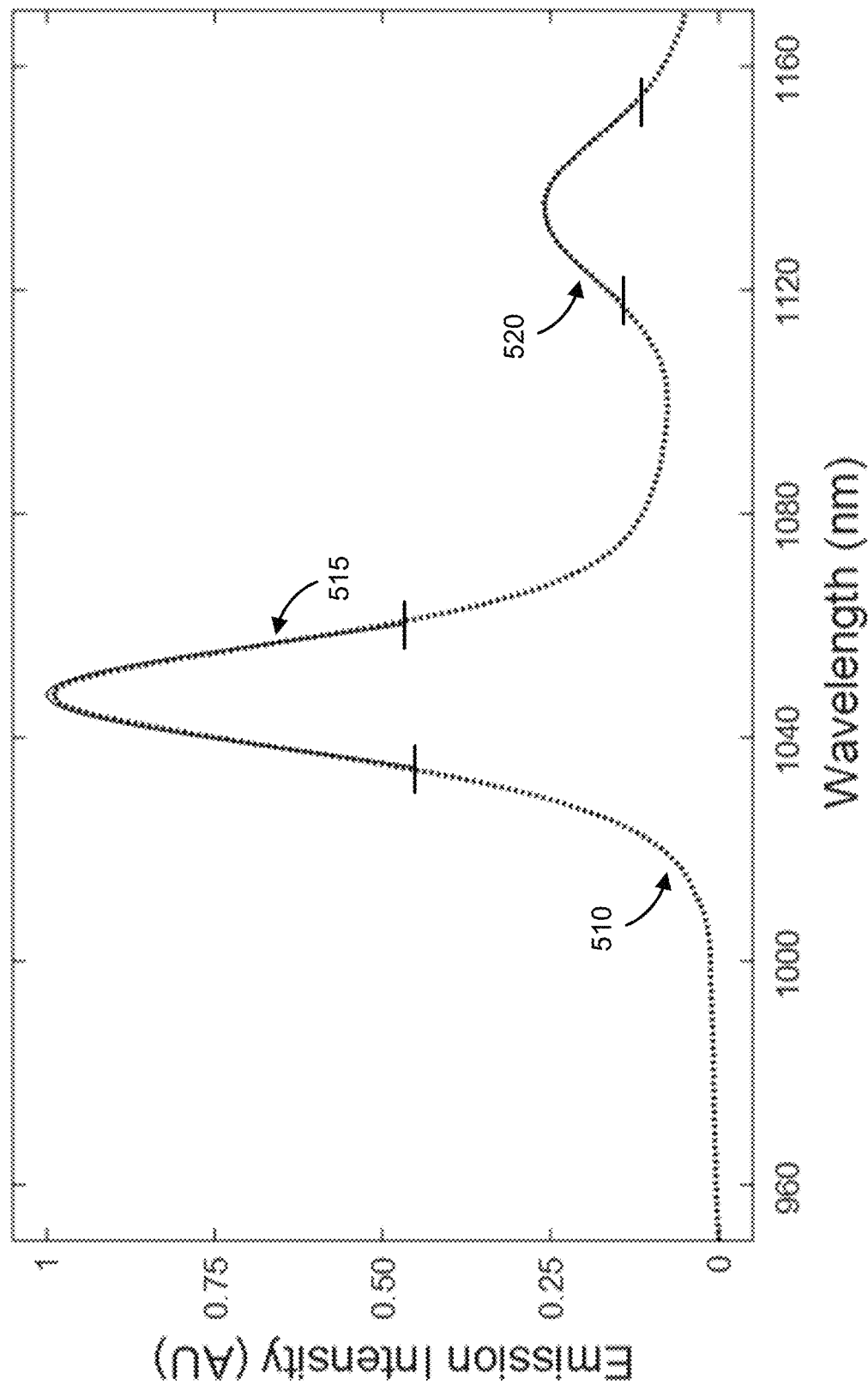
FIG. 5 shows an exemplary emission spectrum acquired from a straight, unstrained coronary catheter whose exterior surface was coated with SWCNT.

An exemplary emission spectrum acquired from a straight, unstrained coronary catheter whose exterior surface was coated with SWCNT 200 is displayed in FIG. 5. Fluorescence excitation light at 660 nm was coupled into the optical core of the double-clad fiber 201 and focused onto the SWCNT-coated sheath by an angle-polished ball lens 202 positioned at the end of the dual clad fiber. Fluorescence emission from the nanotubes was collected through the inner cladding of the same double-clad fiber 201 and focused into an optical spectrometer equipped with a linear InGaAs array detector. The emission spectrum was recorded over the range of 950-1170 nm and shows two prominent peaks at approximately 1050 nm (515), and 1135 nm (520) that are attributed to emission from (7,5) and (7,6) nanotubes, respectively; the fitted portions of each peak are delineated by horizontal tick marks. The peak emission wavelength may be accurately determined by fitting individual emission peaks to a spectral line shape such as log normal 510, Gaussian, or other known line shape functions. Single or multiple functions may be needed to represent the acquired line shape. Polynomial fitting may also be used to determine the peak emission wavelength. Spectral fitting can determine the emission wavelength to subpixel accuracy for the determination of small strains.

Figure 7:
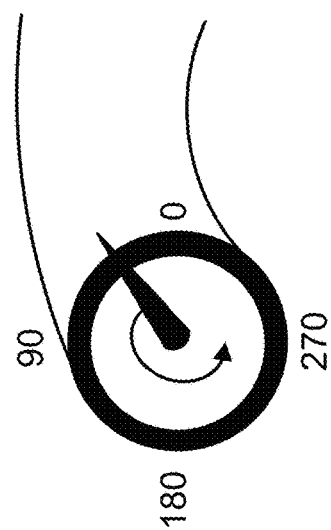
FIG. 7 shows a strain-sensing sheath having a bend with a diagram of light being collected at 0°, 90°, 180°, and 270°.
Figure 6:
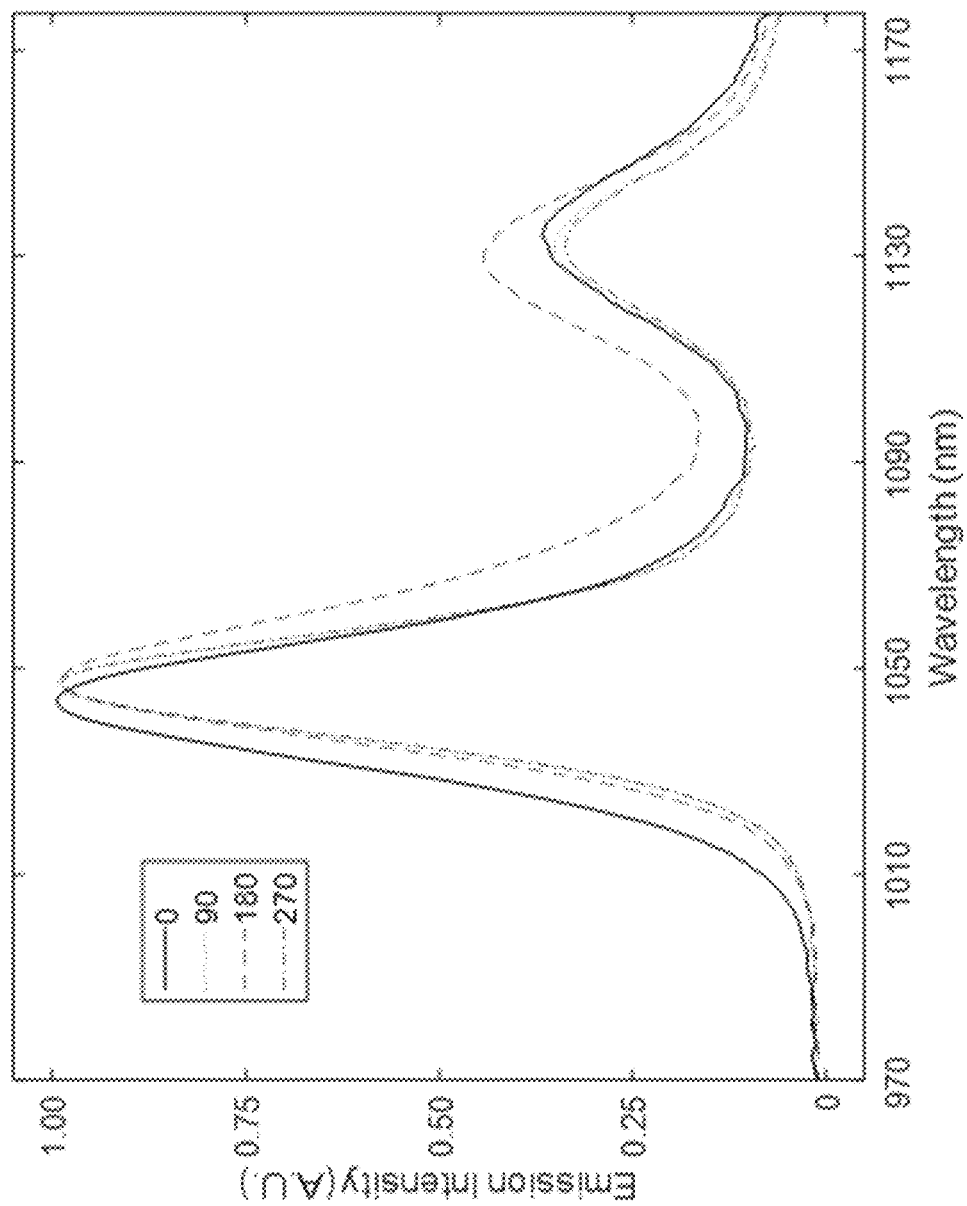
FIG. 6 provides data related to the wavelength-shift of the emission spectrum of single-walled carbon nanotubes embedded in a polyurethane coated intracoronary catheter sheath sampled in-the-plane and orthogonal to the plane of a 45° bend.

Exemplary emission spectra acquired from a strain-sensing sheath are shown in FIG. 6. Spectra were acquired every 90° corresponding to the excitation beam residing in the plane of the bend (0° and 180°) and orthogonal to the plane of the bend (90° and 270°) (see FIG. 7). At the inner curvature (0°), the sheath (nanotubes) experienced a compressive strain resulting in the spectral emission from (7,5) and (7,6) nanotubes to be shifted to lower (blue-shifted) and higher (red-shifted) wavelengths, respectively. At the outer curvature (180°), the sheath was under tensile strain, which resulted in the spectral emission shifting in the opposite direction for (7,5) and (7,6) nanotubes. Spectra acquired in the orthogonal, out-of-plane angles (90° and 270°) were nearly identical and with no appreciable shift in the emission wavelength.

The fluorescence spectra from a strain-sensitive sheath were acquired as the probe helically scanned a sheath that followed a well-defined bend radius. Emission spectra were spectrally fit to a line shape function to determine the peak emission wavelength as function of pullback position and rotation angle as shown in the exemplary data in FIGS. 8A-8C. The frame number (shown on the horizontal axis) is a function of the pullback distance and rotation angle. The extracted emission wavelengths for chiralities (7,5) and (7,6) are shown in FIGS. 8A and 8B, respectively, and their difference (7,6)-(7,5) is shown in FIG. 8C. In the first 200 frames, the coronary catheter is relatively straight, showing little rotational variation in the emission wavelength during scanning. At approximately frame 400, the catheter experiences a constant bend radius of 12 mm, producing a periodic function whose peak wavelength extremes cycle between the maximum tensile and compressive strains. A curvature-dependent wavelength is obtained by averaging several cycles.

A calibration curve that relates the spectral shift to nanotube chirality or multiple nanotube chiralities may be constructed by extracting an averaged emission wavelength for either the compressive or tensile strains as a function of curvature. Note that a mathematical combination of chiralities may increase the strain sensitivity because the strain-induced spectral shifts may act under opposite directions under the same stresses, which is observed for the difference between emission wavelengths of (7,6) and (7,5). FIG. 12B (discussed below) shows a calibration curve that maps the spectral shift (peak separation) relative to the radius of curvature. As seen in FIG. 12B and discussed further below, this relationship is linear and sensitive over a range of curvatures that is needed to detect the 3D geometry of the catheter.

Figure 9:
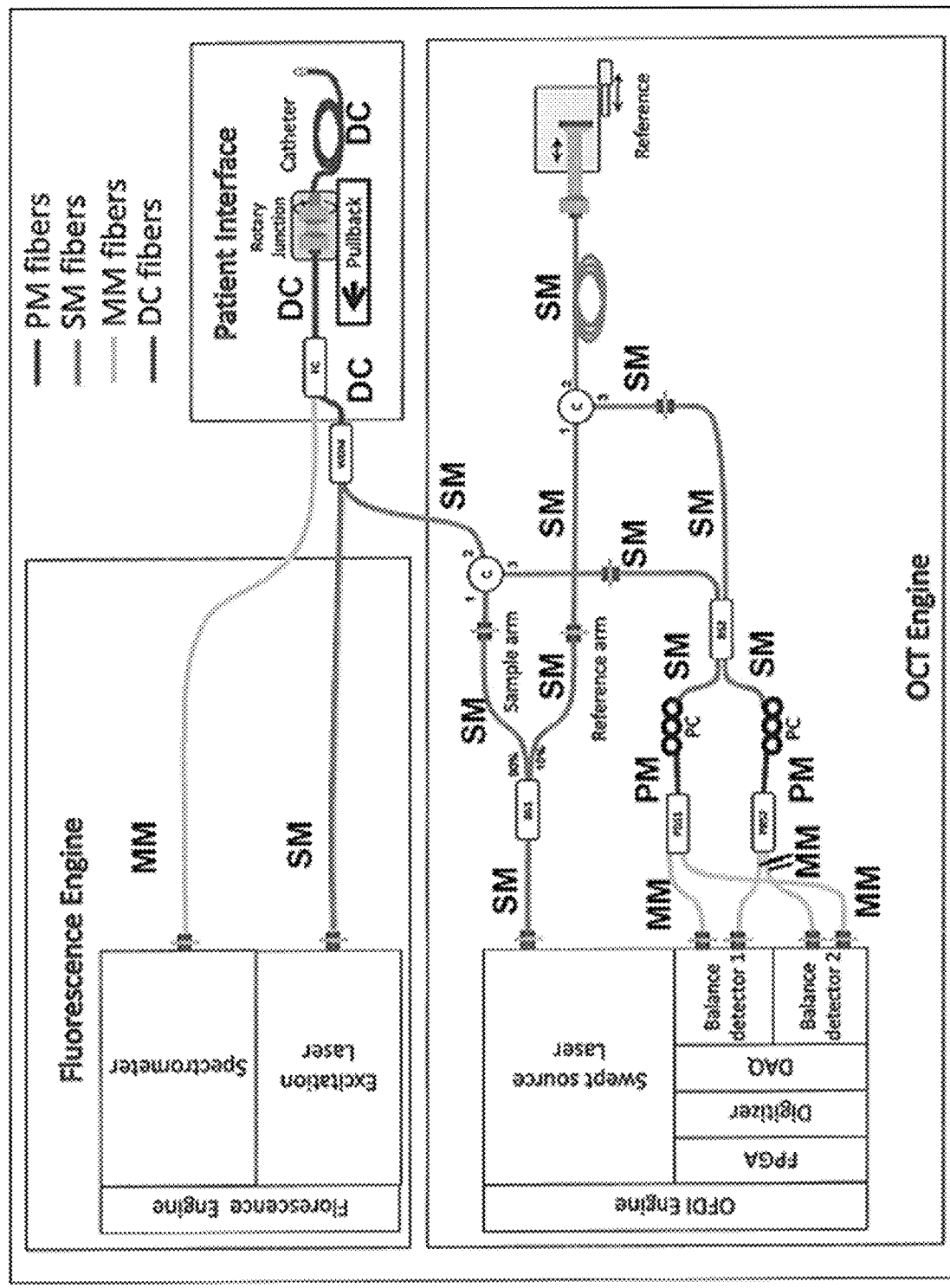
FIG. 9 is a block diagram of an exemplary embodiment of an apparatus for reconstructing the 3D shape of a luminal object such as vessel according to the present disclosure.

FIG. 9 is a schematic of an exemplary embodiment of a three-dimensional shape sensing system, which is comprised of two subunits: (1) an optical frequency domain imaging (OFDI) engine that acquires microstructural images of tissue, and (2) a fluorescence engine that provides the shape-sensing capabilities. The OFDI system is built around a Swept Source Engine from AXSUN Technologies. In addition to a 100 kHz swept laser, the OCT Axsun engine contains high-speed data acquisition electronics which are optimized for acquisition of OFDI data using an Ethernet interface. The swept wavelength light from the Axsun laser is coupled to a single mode (SM) fiber-based beam splitter (BS1) which directs 90% of the signal to the sample arm and 10% to the reference arm. After passing through a circulator (C), the sample arm light is combined with the fluorescence excitation beam using a wavelength division multiplexer (WDM) unit. The combined excitation and OCT laser beam is coupled to a double clad (DC) fiber coupler (FC) which is attached to a custom-fabricated rotary junction. A DC fiber catheter is attached to the rotating part of a rotary junction (RJ). At the end of the catheter, a ball lens is fabricated and polished to direct the light signals towards the sample; in one particular embodiment a custom fiber catheter is placed within a flexible transparent sheath. In certain embodiments the outside of the sheath is coated with carbon nanotubes for strain sensing, although in other embodiments the strain-sensing material may have a different location (e.g. embedded in the sheath material or on the inside of the sheath). During imaging, the catheter is rotated and the rotating catheter is pulled back within the sheath to generate helical scans.

For OFDI imaging, back-reflected light from the sample and reference surfaces is directed by corresponding circulators (C) toward a beam splitter (BS2) where these signals interfere with each other. The use of polarization beam splitters (PBS1, PBS2) and polarization controllers (PC) after the beam splitter BS2 allows implementation of a polarization diverse detection scheme that avoids image artifacts that might otherwise arise due to polarization changes induced by the optical fiber in the rotating catheter. Light from the polarization maintaining (PM) fibers is detected using two balanced detectors composed of four diode receivers. The digitized signal from the photodiodes is then processed on a field-programmable gate array (FPGA) board including wavelength re-mapping and Fourier transformation to obtain a depth-resolved OFDI signal (A-line). A-lines collected during every rotation of the optical beam are compressed by the Axsun engine to a JPEG format and transferred to a workstation via an Ethernet cable for real-time circumferential display and data storage.

On the strain sensing side, the fluorescence signal from the carbon nanotubes is collected through the cladding of the DC fiber of the catheter. After passing through the RJ, this signal is sent to the spectrometer by the fiber coupler. In one embodiment, the spectrometer includes an input slit, guiding optics, a grating, and a super-cooled, low noise linear response camera. The signal from the spectrometer is used to determine the strain within the sheath.

Figure 10:
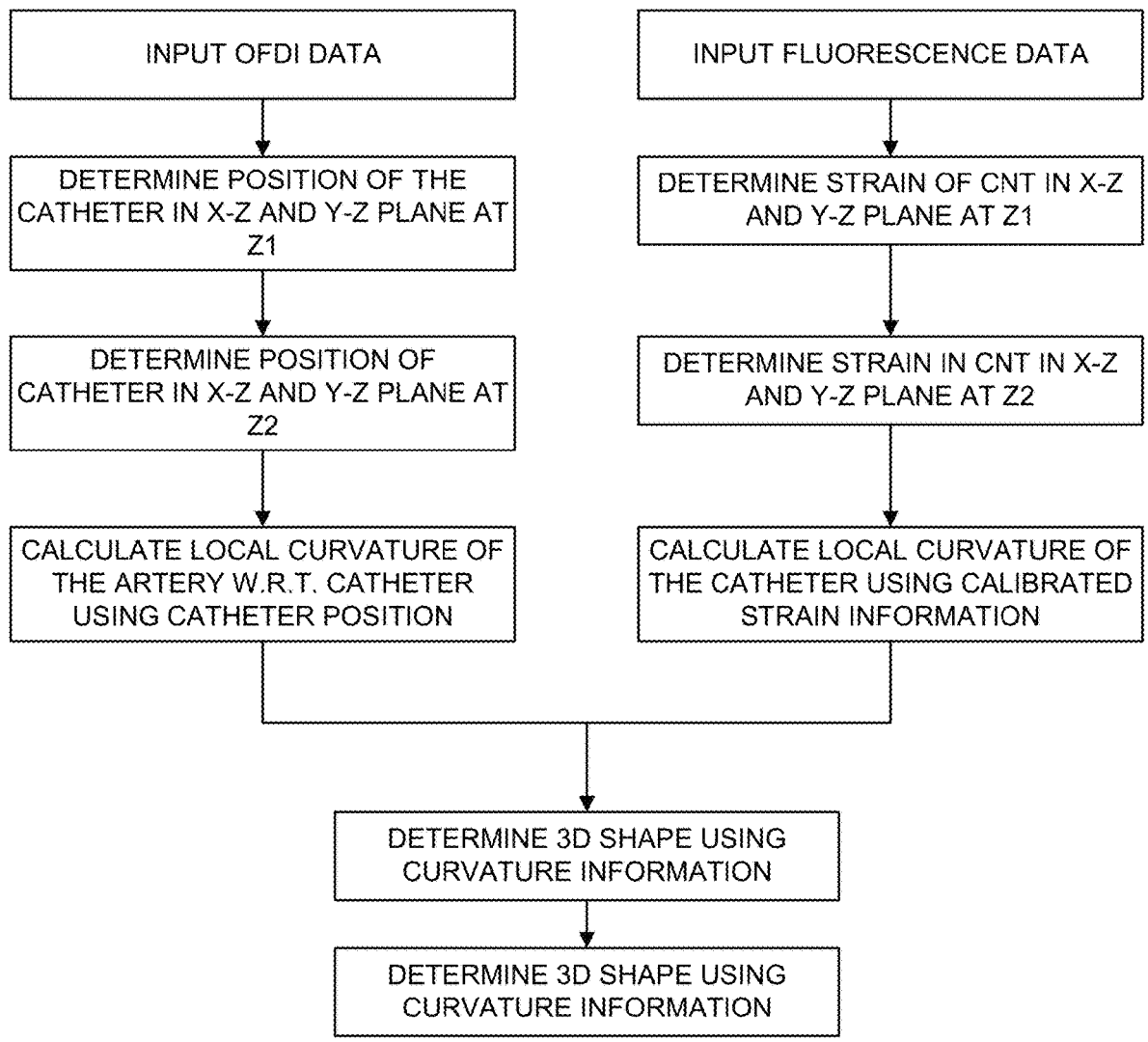
FIG. 10 is a schematic of the exemplary process for reconstructing the three-dimensional shape of a luminal object from a combination of OCT and spectroscopic data acquired at a known pullback position and rotational angle.

FIG. 10 describes the algorithm for 3D reconstruction using one of the exemplary embodiments. In various embodiments, full 3D reconstruction is based on input from two channels, namely a structural optical (e.g. OFDI) imaging channel and a strain sensing channel. First, the position of the catheter with respect to the artery wall is determined either manually, or semi-automatically or automatically using image analysis algorithms to detect said position, at two different locations, Z1 and Z2, in two different planes, x-z and y-z. Using these values, the curvature of the catheter with respect to the artery wall is calculated. Further, using the fluorescence data from carbon nanotubes, strain is calculated in the same planes (x-z and y-z) as curvature was calculated from OFDI data, and the measured strain values are converted to curvature using the calibration data. This process gives the curvature of the catheter itself in two planes. The actual curvature of the artery in different orthogonal planes can be calculated by adding the curvature of the catheter and the curvature of the artery with respect to the catheter in these planes. Once the curvature of the artery is known in two planes, the 2D shape is calculated in the orthogonal planes. The 3D shape can be generated from the shapes in the two orthogonal planes using software such as the commercially-available IVUSAngio tool.

The process of measuring ESS from these data is extremely time-intensive, necessitating a unique catheterization lab process and biomedical engineering expertise. The angiogram must be acquired using a biplane/isocentric configuration so that the artery can be accurately reconstructed in three dimensions, a requirement that is impractical for most PCI labs. 3D reconstruction is laborious, as the artery's centerline must be derived from the angiogram, the OCT or IVUS lumens segmented, and the lumen centroids co-registered to the centerline. The present disclosure provides methods and apparatus to bypass resource- and time-intense limitations of ESS computation by providing a single device that can automatically and in real-time determine the 3D structure of the arterial lumen, calculate the detailed local ESS patterns, and display them in concert with anatomic characterization by OCT. By removing the barriers to ESS computation and providing a practical means for obtaining this measurement in real-time or near real-time in the catheterization lab, this advance can make it possible for the first time to use ESS to guide coronary intervention and provide optimal CAD management at the point of care.

These data may be processed to automatically determine the 3D centerline of the catheter. In combination with automated luminal segmentation, this technology can allow the luminal contours to be rapidly mapped to the catheter's centerline to reconstruct an anatomically correct 3D representation of the coronary artery.

Figure 11:
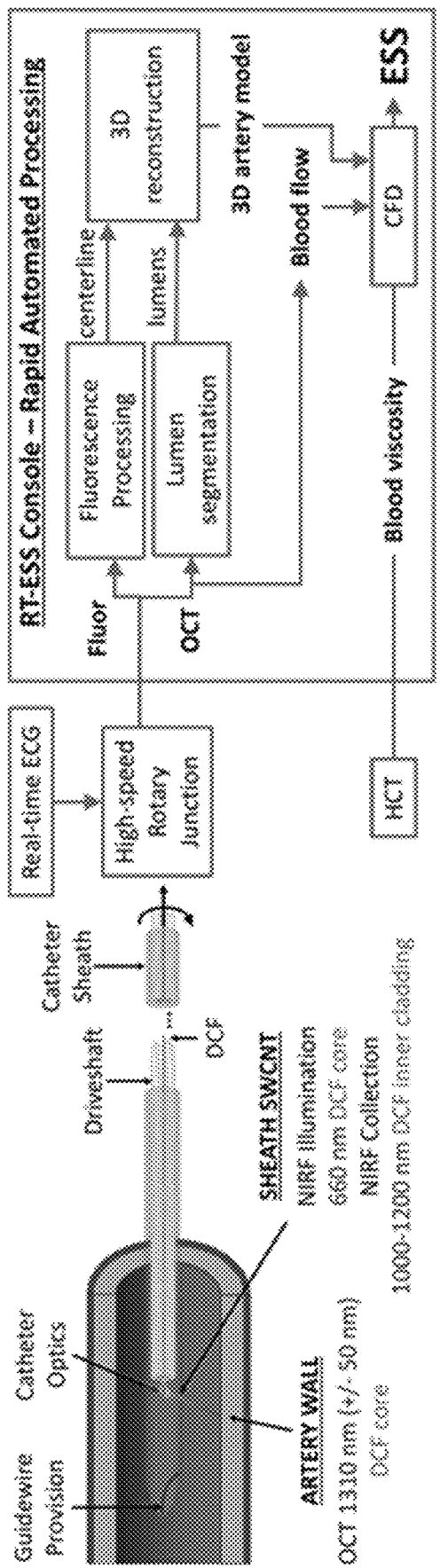
FIG. 11 shows a schematic of the RT-ESS catheter and imaging console. ECG: electrocardiogram; DCF: double-clad fiber; CFO: computational fluid dynamics; HCT: hematocrit; ESS: endothelial shear stress; OCT: optical coherence tomography; NIRF: near infrared fluorescence; SWCNT: single-walled carbon nanotubes; Fluor: fluorescence.

FIG. 11 depicts a high-level schematic of an embodiment of an RT-ESS system and catheter. In some embodiments, the catheter may be identical to an existing clinical 2.6F intracoronary DCF-based OCT-NIRF catheter and, in particular embodiments, the inner surface of the outer sheath may be functionalized with a thin layer of fluorescent SWCNTs for which the emission spectra are shifted when placed under strain. OCT (1310±50 nm) and SWCNT fluorescence excitation light (660 nm) can be transmitted through the core of the DCF within the multimodality catheter. Under radiographic guidance, the catheter may be advanced over a guide wire through a guide catheter until its imaging tip is located distally to the target coronary location. A non-occlusive radiocontrast flush can be injected through the guide catheter, displacing blood from the artery's imaging field. Light from the focusing optics at the distal tip of the catheter can then be helically scanned via a high-speed DCF rotary junction (in one embodiment the rotation rate may be 800 kHz and the translation rate in a range of 10-20 cm/s), gated to diastole via synchronization with real-time ECG. OCT light from the artery wall will return through the DCF's core. NIR SWCNT fluorescence (1000-1200 nm) from the entire catheter's sheath can be simultaneously collected through the DCF's larger inner cladding. OCT and fluorescence light may be separated inside the RT-ESS console and detected and digitized separately. OCT images may be automatically segmented to extract each cross-section's lumen. Automated processing of the peak shifts in the SWCNT fluorescence spectra will determine the catheter's 3D centerline. An anatomically correct 3D artery model will then be reconstructed by placing the lumens onto the intrinsically co-registered catheter's centerline. To compute artery-specific flow, a known volume of contrast can be injected through the guide catheter and while acquiring another OCT scan. The time between OCT images of the leading and trailing edges of the bolus can then be used to estimate blood flow. Blood viscosity can be determined from the patient's hematocrit (HCT). The 3D artery model, blood flow, and blood viscosity may be input into a highly optimized, parallel CFD simulation, the output of which can provide an ESS map.

In certain embodiments, OCT is employed as the intravascular anatomic imaging technology because it is a standard imaging technique for assessing plaque morphology and the adequacy of stent deployment in the catheterization lab. Furthermore, its high resolution and contrast can provide the most accurate geometry and detailed ESS maps. Because OCT images are acquired with a non-occlusive radiocontrast flush to remove blood from the field of view, such images are also very amenable for automated analysis. A recent study has shown that OCT measures of plaque extent and free wall arc are highly correlated to IVUS measures of plaque burden, which is significant because this metric is associated with future coronary events.

Figure 12A:
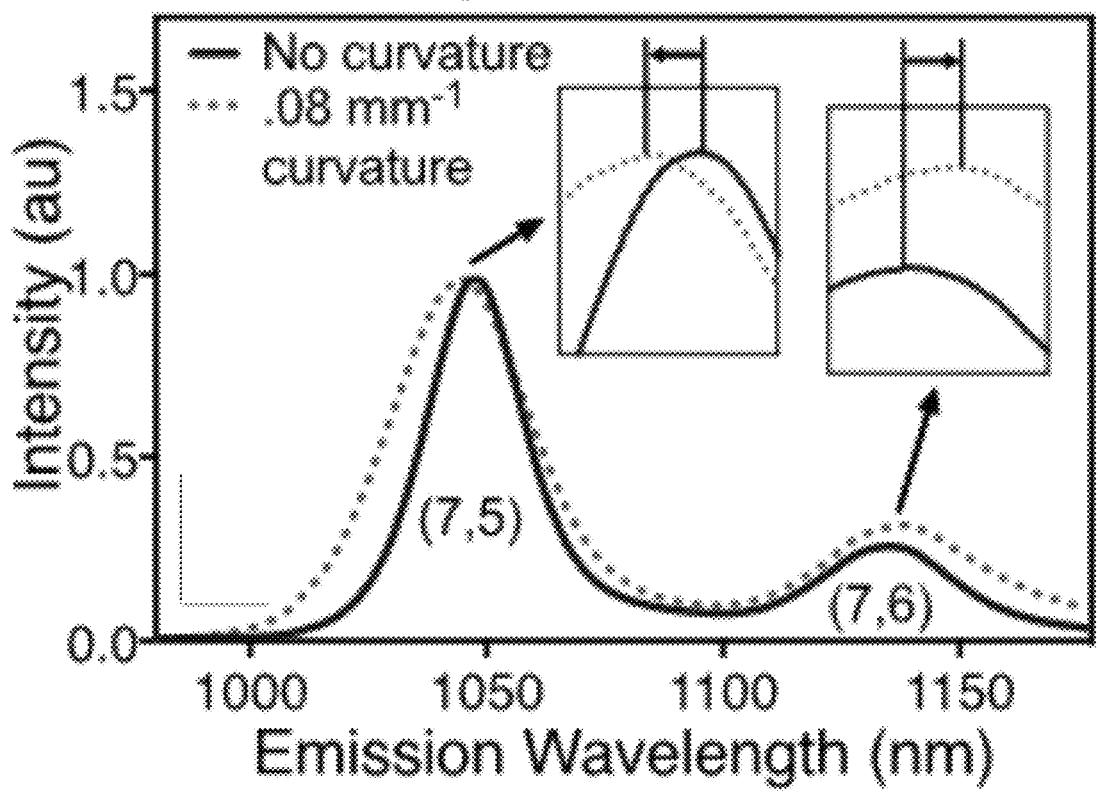
FIG. 12A shows fluorescence spectra of (7,5) and (7,6) SWCNT on the catheter's sheath at 0 (solid line) and 0.08 $mm^{-1}$ (dotted line) curvatures showing compressive strain-induced blue and red wavelength shifts, respectively.
Figure 12B:
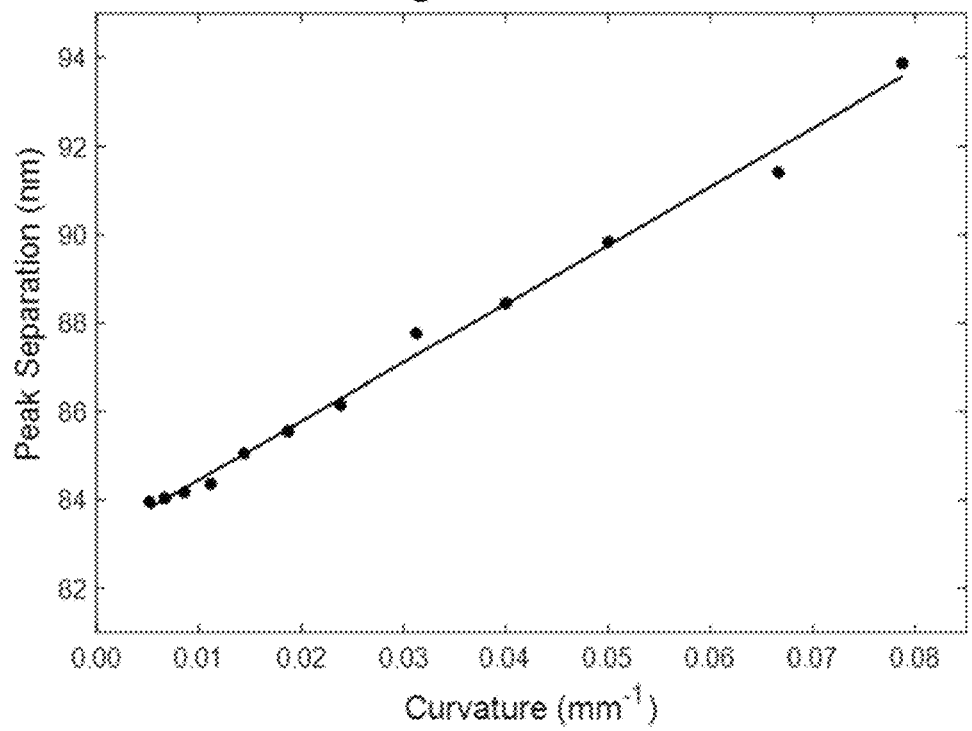
FIG. 12B shows a scatter plot of (7,5) and (7,6) peak separations vs. sheath curvature.

The fluorescence spectra of a catheter having a strain-sensitive sheath (made by applying SWCNTs to the sheath as described above) coupled thereto were measured at various curvatures to determine the relationship between curvature and SWCNT fluorescence peak separation, as shown in FIGS. 12A-12B. Fluorescence excitation light (660 nm) was coupled into the catheter's DCF core and focused onto the coated sheath by an angle-polished ball lens at the end of the fiber. Fluorescence emission from the nanotubes was collected through the inner cladding of the DCF and detected by a spectrofluorometer. FIG. 12A (solid line) shows the fluorescence spectrum of the (7,5) and (7,6) SWCNT coating on a straight catheter, demonstrating two NIR emission peaks at approximately 1050 nm and 1140 nm, respectively. The catheter was then bent and its optics were directed to collect fluorescence in-plane with the bend from the inner curvature of the sheath. At this location, the nanotubes experienced compressive strain, causing the fluorescent peaks to broaden and spectrally shift away from one another (FIG. 12A, dotted line). Opposite shifts occurred for tensile strain (not shown). The (7,5) and (7,6) peak separations were measured as a function of varying sheath curvatures by fitting the individual peaks with a Gaussian line shape function. As seen in FIG. 12B, this relationship was linear and sensitive over a range of curvatures that is needed to detect the 3D geometry of the catheter. This data shows that carbon nanotube fluorescence can be used to detect the curvature of the RT-ESS catheter.

SWCNT Catheter-Based Shape Sensing and 3D Artery Reconstruction

Figure 13C:
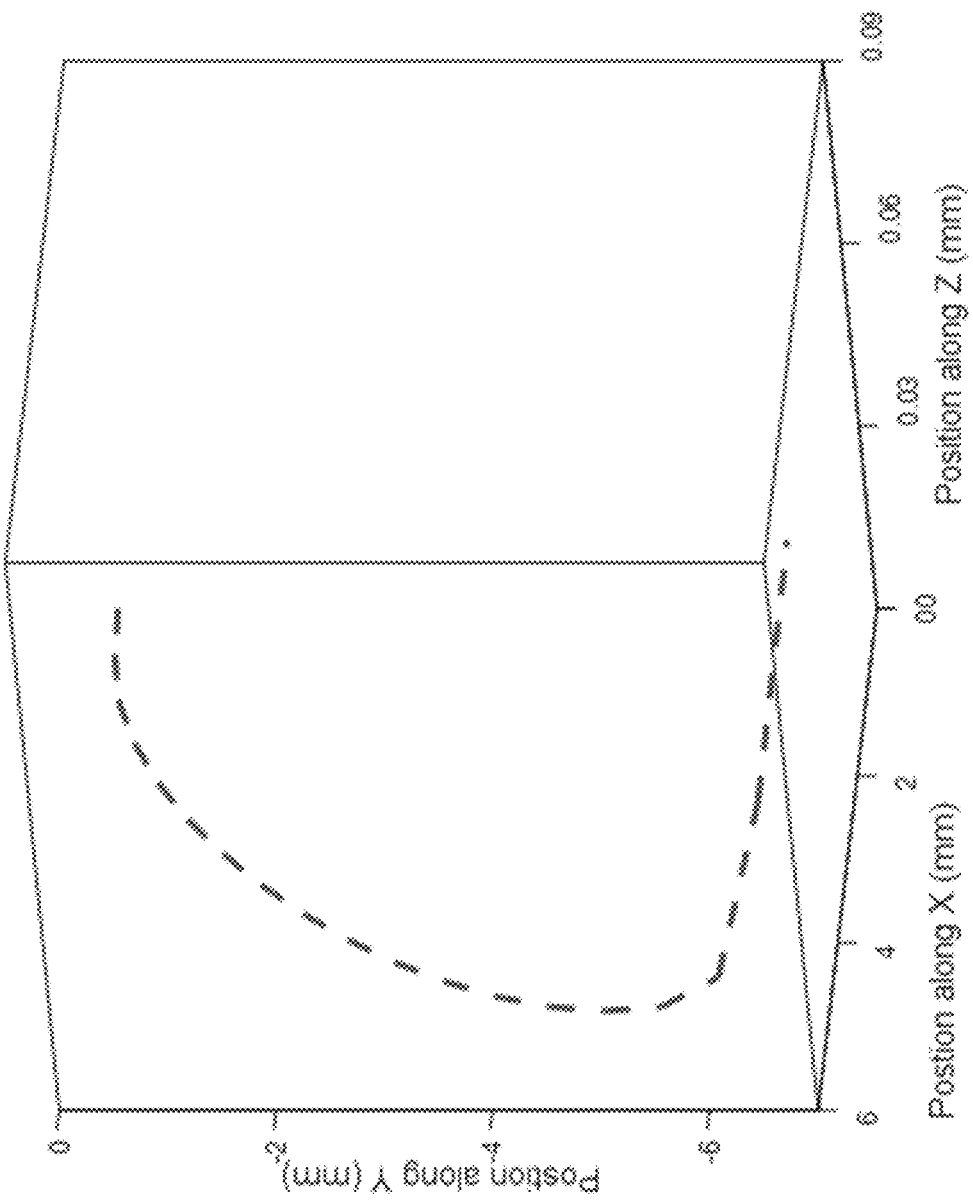
FIG. 13C shows a centerline of a 3D reconstruction relative to X, Y, and Z axes.

To test the principle of SWCNT catheter-based shape sensing for 3D reconstruction of a coronary artery, the aforementioned catheter was connected through a DCF rotary junction to an OCT-NIRF system, modified by the addition of custom wavelength-separating optics and NIR fluorescence spectral detection. The catheter was then inserted into a phantom of a coronary artery lumen, which was 3D-printed using a lumen centerline from a human dataset (FIG. 13A). The catheter's inner optics were helically scanned along the phantom's lumen (1 mm/s pullback and 1 Hz rotation), simultaneously grabbing OCT A-lines and fluorescence spectra from the catheter's sheath at every angular (θ) and lateral (z) location. The OCT dataset was processed by segmenting the lumen. The fluorescence spectra were fit and peak separations were used to create a curvature map at each θ-z scan position. The catheter's curvature map was converted to a 3D catheter centerline by solving modified Frenet-Serret equations. The OCT lumens for each frame were subsequently superimposed on the catheter's centerline, converted into a 3D mesh, and rendered (FIG. 13B). The 3D centerline of the phantom artery's lumen measured using the SWCNT catheter (FIG. 13B) closely matched the known 3D centerline of the phantom, with a Pearson's Correlation Coefficient (PCC) of 0.84. FIG. 13C shows a centerline of the 3D reconstruction relative to X, Y, and Z axes. This data shows that OCT-NIRF and a SWCNT catheter can be used to automatically and accurately measure the 3D shape of a coronary artery.

SWCNT Fluorescence Efficiency

To recover the shape of the catheter, embodiments of a clinical RT-ESS system may need to acquire at least 8 spectra per circumferential scan of the catheter's optics. Assuming a frame rate of 800 Hz, spectra will be digitized at approximately 6.5 kHz (150 µs integration time), which may be facilitated by the use of a high-speed imaging spectrograph. Using relatively crude and low concentration SWCNT preparations, an adequate fluorescence signal strength of ~2000 counts has been achieved during a 100 ms integration time with 10 mW of optical power on the sheath. Applying an SNR analysis and assuming a safe excitation power of 50 mW, in various embodiments an approximately 100-times higher SWCNT fluorescence intensity may be needed to facilitate faster acquisition rates, a factor that may be gained by increasing nanotube concentration and alignment as described further below. These results show the feasibility of achieving the SWCNT fluorescence intensity required to measure the catheter's shape at RT-ESS acquisition rates.

Although data disclosed herein demonstrates that a SWCNT-functionalized, mechanical scanning OCT catheter can create accurate 3D coronary artery models, in various embodiments an improved device suitable for use in humans may be provided. In one embodiment, nanotubes may be coated on the inside of the sheath to shield the SWCNT from body fluids, although doing so may be challenging when the catheter includes a closed distal tip. In other embodiments, the nanotubes may be coated at higher concentrations than used in the example above; the nanotubes may be dispersed to maintain their fluorescence properties; and the nanotubes may be aligned along the catheter's axis to optimize emission intensity and strain sensitivity. In further embodiments, the coating may be thin, tightly-toleranced, and robust so that it is not effaced by the rotating driveshaft.

Figure 14:
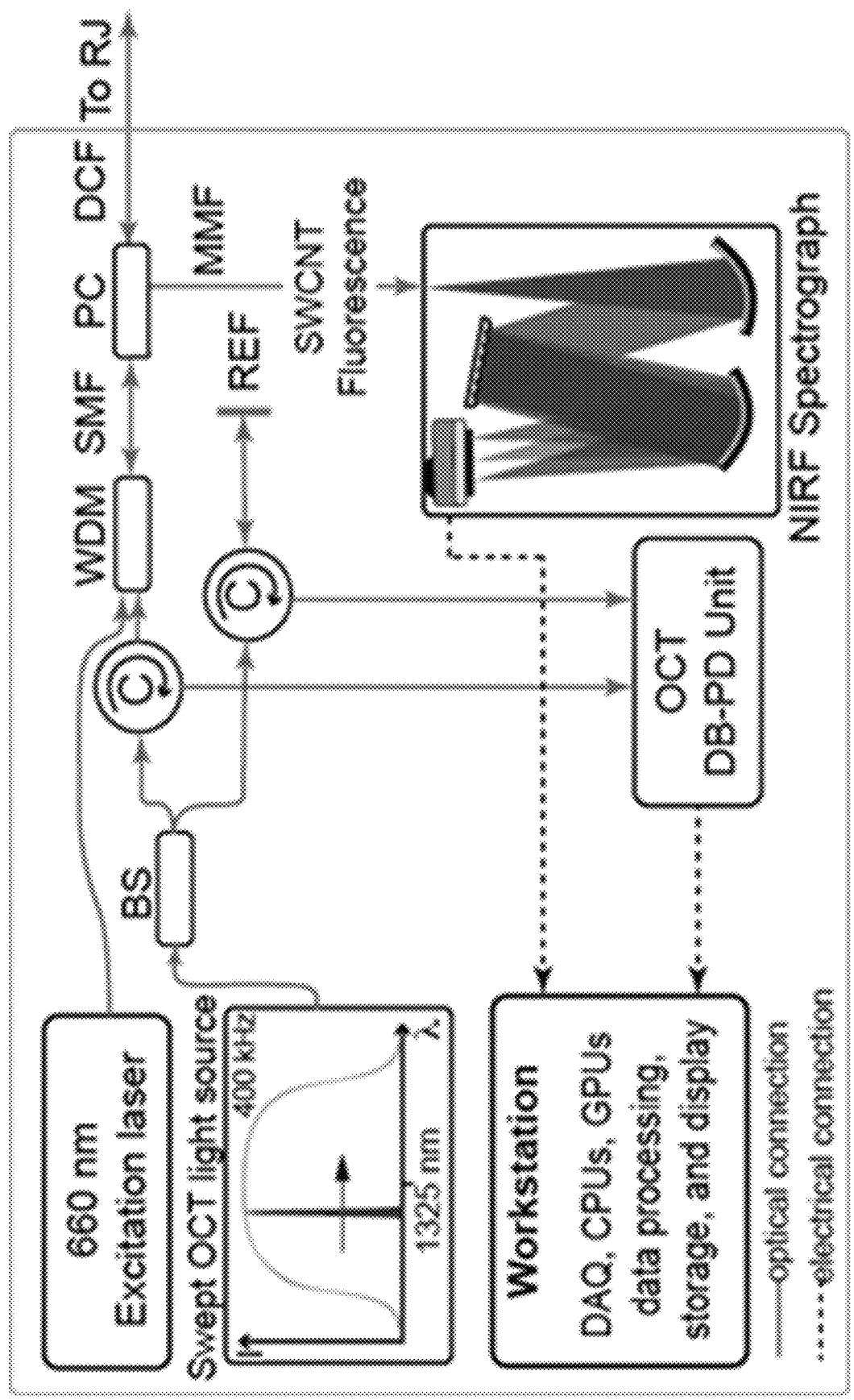
FIG. 14 shows a schematic of an RT-ESS console in which: RJ: rotary junction; C: circulator; BS: beam splitter; WDM: wavelength division multiplexer; PC: power combiner; REF: reference arm; DB-PD-dual-balanced, polarization-diverse; ADC: analog/digital converter; CPU: central processing unit; GPU: graphical processing unit.

In various embodiments, the RT-ESS console may be capable of one or more of: 1) acquiring high speed OCT images; 2) detecting and digitizing SWCNT fluorescence spectra; and 3) rapidly processing these signals to compute ESS. The target time from acquiring the OCT data to ESS may be 1 minute (optimal) to 3 minutes (minimal), either of which is a sufficiently short time that it can be completed during a catheterization lab procedure. FIG. 14 shows a schematic of an embodiment of a RT-ESS console.

OCT light may be provided by a wavelength-tuned laser that uses a MEMS-based Fabry-Perot cavity to sweep over a ~100 nm bandwidth at 200 kHz A-line rate with a duty cycle of 50%. To acquire cross-sections at 800 Hz (512 A-lines/image), the A-line frequency may be doubled to 400 kHz by buffering (2×) the laser using a fiber optic delay line terminated by a Faraday mirror. A buffer optical amplifier may be utilized to normalize output power. The OCT interferometer may use a standard circulator-based Mach-Zehnder configuration with a computer-controlled reference arm path length. 660 nm SWCNT excitation light can be combined with OCT sample arm light through a WDM; both may then be coupled to the core of a DCF via a power combiner.

Fluorescent light from the sheath returning through the DCF's inner cladding may be diverted through the power combiner to a MMF that will illuminate a high-speed NIRF (6000 spectra/s) InGaAs imaging spectrograph. The OCT spectral interferometric signal can be detected using a dual-balanced polarization diverse detection unit. Detector output may be digitized at 12 bits, sampled by a doubled k-clock provided by the laser. Interferometric OCT data may be transferred to a GPU, converted into OCT images, processed, displayed, and stored to high-speed solid-state drives (SSDs).

In various embodiments, a rotary junction such as that used with multimodality DCF-based devices, the use of which has been demonstrated clinically, may be used. To avoid motion artifacts in the OCT dataset, image acquisition and catheter rotational rates may be increased so that the entire pullback can be accomplished during a single diastolic cycle when the catheter and artery are stationary. Initiation of the catheter's helical scan may be synchronized to the diastolic trigger of a real-time ECG recording. Assuming a maximum heart rate of 100 bpm, and given that diastole is ~50% of the cardiac cycle, an average 5 cm pullback may take ~0.3 s. Given an image spacing of 200 µm, 250 images may be captured in 0.3 µs, requiring a rotational rate of ~800 Hz.

Acquired spectra may be fit to a Gaussian function to determine (7,5) and (7,6) SWCNT fluorescence peak separations, which can be converted to curvature at each θ-z scan position. The centerline may be computed by solving Frenet-Serret equations describing the 3D catheter's path.

Thus, in various embodiments the invention includes an apparatus for determining a shape of a luminal sample. The apparatus includes a catheter that is disposed within a strain-sensing sheath. The strain-sensing sheath is associated with strain-sensing molecules such that changes in the shape of the strain-sensing sheath lead to strain on the sheath that can be detected spectroscopically. The catheter/sheath combination may be inserted into a luminal structure such as an artery and the shape of the artery is determined by measuring differences in strain along the sheath. In particular, a lens associated with the catheter may be rotated inside the sheath while also being translated (e.g. using a pullback), producing a helical travel. While the lens moves (e.g. helically) it collects data from the sheath (e.g. from molecular spectroscopic data) that indicates strain and may also collect structural information (e.g. OCT) which may be used to determine the 3D shape of the luminal sample. The spectroscopic data from the sheath can be combined with the structural information to determine the overall shape of the luminal sample, e.g. essentially producing a wireframe model of the central axis of the luminal sample.

The strain-sensing molecules associated with the sheath are selected based on having a detectable spectral shift in response to changes in strain. Thus, in certain embodiments the strain-sensing sheath has nanotubes (e.g. single-wall carbon nanotubes, SWCNTs) associated with the sheath, where the nanotubes undergo a spectral shift as a result of a change in strain.

To detect the spectral shift in the strain-sensing molecules, the catheter has a lens (e.g. a ball lens) attached to its end, where the lens is configured to rotate and translate within the strain-sensing sheath. To facilitate rotation of the lens, the catheter in some embodiments is optically coupled to the structural optical system and the molecular spectroscopic system using a rotary junction. The lens is configured to transmit light at an angle (e.g. a right angle) relative to the long axis of the catheter so that light is emitted and collected from the side walls of the sheath and the luminal structure into which the sheath has been inserted.

As the lens rotates and translates through the sheath, light is emitted from the lens and collected by the lens to collect data for determining strain and for determining structural information. The light from the molecular spectroscopic system is emitted by the lens and interacts with the strain-sensing molecules associated with the sheath and light returned from the sheath (e.g. in the form of fluorescence) is collected by the lens.

The returned light is analyzed spectroscopically to identify any spectral shift(s) which are indicative of changes in strain. Strain can be determined at two different locations along the axis of the sample (referred to as Z1 and Z2, e.g. see FIG. 10), for example by determining strain in an x-z plane and a y-z plane at each location. From this information a local curvature of the catheter and sheath can be determined (with reference to calibration information). The molecular spectroscopic system may be based on fluorescence spectroscopy, Raman spectroscopy, or absorption spectroscopy.

Light from the structural optical system (e.g. OCT) is also emitted through the lens as the lens/catheter moves (e.g. helically) through the sheath. Light returned from the sample is collected by the lens and directed to the structural optical system. The returned light can be used to determine the position of the catheter, for example in an x-z plane and a y-z plane at each location Z1 and Z2. From this a local curvature of the luminal structure can be determined relative to the catheter (to the extent that the catheter does not exactly follow the contours of the luminal structure).

The operation of the catheter and optical data collection may be performed by one or more controllers, e.g. computer systems each including one or more processors/microprocessors, memory, storage, input, output, and communications capabilities. The controller(s) may control operations such as the rotation of the lens, emitting and collecting light from the lens, and processing of data. The controller(s) may be coupled to, e.g. may be in communication with, the structural optical system and/or the molecular spectroscopic system in order to perform functions related to these systems. In particular, the controller may carry out steps to perform operations according to embodiments disclosed herein.

In various embodiments the sheath includes a sheath wall. The sheath wall may be associated with strain-sensing molecules (e.g. SWCNTs). In various embodiments, the strain-sensing molecules may be on an inside face of the sheath wall, an outside face of the sheath wall, or may be embedded within the sheath wall. In other embodiments, the strain-sensing molecules may be associated with one or more wires that are then attached to the sheath wall, e.g. on the outside face. In certain embodiments the strain-sensing sheath may be disposed within another, outer sheath (e.g. if the strain-sensing molecules are located on the outer wall of the strain-sensing sheath then by disposing the strain-sensing sheath within another, outer sheath this keeps the strain-sensing molecules away from the luminal sample, i.e. away from the body of the subject).

Figure 15:
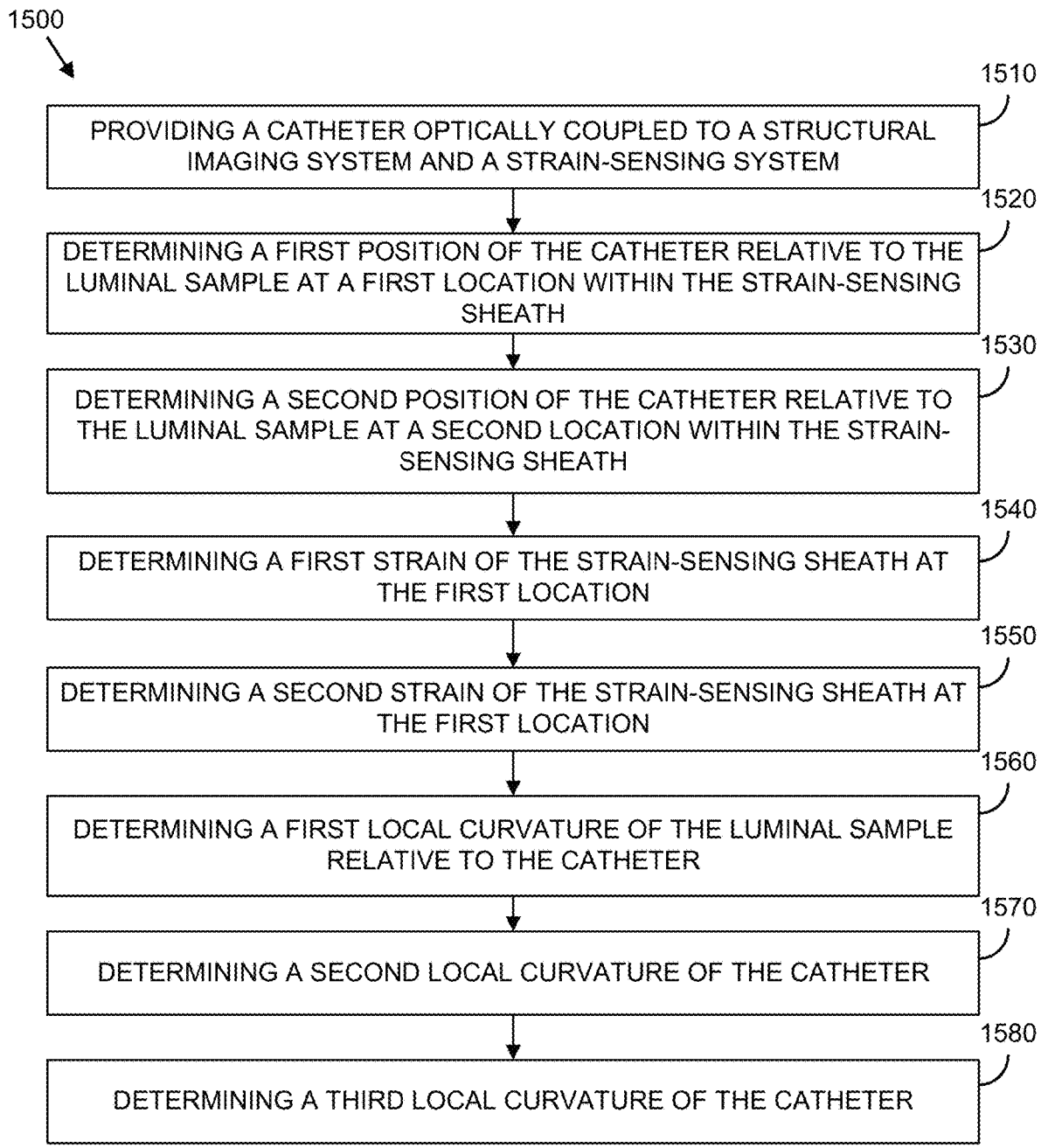
FIG. 15 is a flow chart of an example process for determining a shape of a luminal sample.

FIG. 15 is a flow chart of an example process 1500 for determining a shape of a luminal sample. The process 1500 includes a step of providing a catheter optically coupled to a structural imaging system and a strain-sensing system (step 1510). The catheter may include a lens and the catheter may be disposed within a strain-sensing sheath such that the lens rotates and translates within the strain-sensing sheath. The process 1500 may also include a step of determining a first position of the catheter relative to the luminal sample at a first location within the strain-sensing sheath (step 1520). This and other steps may be carried out by a controller coupled to the molecular spectroscopic system and the structural optical system. The process 1500 may further include a step of determining a second position of the catheter relative to the luminal sample at a second location within the strain-sensing sheath (step 1530), where the first location is different from the second location. The process 1500 may also include steps of determining a first strain of the strain-sensing sheath at the first location (step 1540) and determining a second strain of the strain-sensing sheath at the second location (step 1550). The process 1500 may also include a step of determining a first local curvature of the luminal sample relative to the catheter (step 1560) between the first location and the second location based on determining the first position and the second position of the catheter. The process 1500 may further include a step of determining a second local curvature of the catheter (step 1570) between the first location and the second location based on determining the first strain and the second strain of the strain-sensing sheath. The process 1500 may additionally include a step of determining a third local curvature of the luminal sample (step 1580) between the first location and the second location based on determining the first local curvature and the second local curvature. Process 1500 of FIG. 15 may be used in conjunction with the methods and apparatus disclosed herein.

Figure 16:
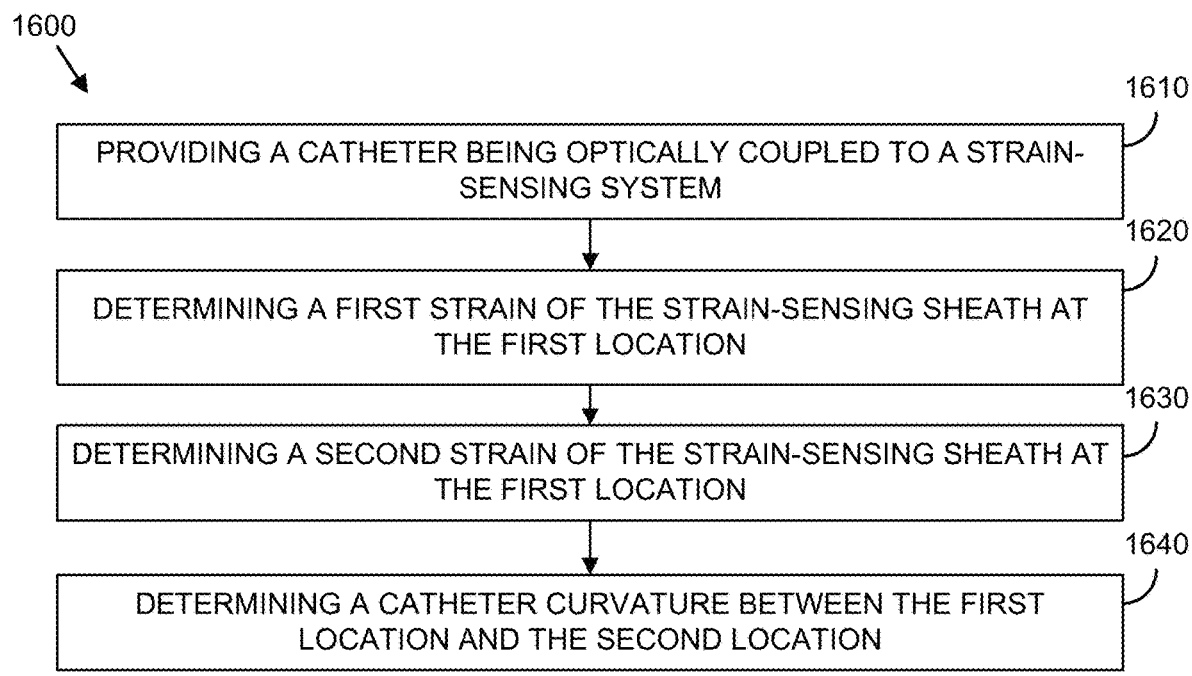
FIG. 16 is a flow chart of an example process for determining a shape of a catheter disposed within a sheath.

FIG. 16 is a flow chart of an example process 1600. The process 1600 includes a step of providing a catheter being optically coupled to a strain-sensing system (step 1610). The catheter may include a lens and the catheter may be disposed within a strain-sensing sheath such that the lens rotates and translates within the strain-sensing sheath. The process 1600 may also include a step of determining a first strain of the strain-sensing sheath in an x-z plane and a y-z plane at a first location (step 1620) within the strain-sensing sheath. This and other steps may be carried out by a controller coupled to the molecular spectroscopic system. The process 1600 may further include a step of determining a second strain of the strain-sensing sheath an x-z plane and a y-z plane at a second location (step 1630) within the strain-sensing sheath, where the first location is different from the second location. The process 1600 may also include a step of determining a catheter curvature between the first location and the second location (step 1640) based on determining the first strain and the second strain of the strain-sensing sheath. Process 1600 of FIG. 16 may be used in conjunction with the methods and apparatus disclosed herein.

It will be apparent to those skilled in the art that numerous changes and modifications can be made in the specific embodiments of the invention described above without departing from the scope of the invention. Accordingly, the whole of the foregoing description is to be interpreted in an illustrative and not in a limitative sense.

What is claimed is:

1. An apparatus for determining a shape of a luminal sample, comprising:
   a catheter comprising a lens,
     the catheter disposed within a strain-sensing sheath such that the lens rotates and translates within the strain-sensing sheath;
   a structural imaging system optically coupled to the catheter;
   a strain-sensing system optically coupled to the catheter; and
   a controller coupled to the strain-sensing system and the structural imaging system,
     the controller, using the structural imaging system, configured to:
       determine a first position of the catheter relative to the luminal sample at a first location within the strain-sensing sheath, and
       determine a second position of the catheter relative to the luminal sample at a second location within the strain-sensing sheath,
         the first location being different from the second location,
     the controller, using the strain-sensing system, configured to:
       determine a first strain of the strain-sensing sheath at the first location based on fluorescence spectroscopy of a first strain-sensing molecule associated with the strain-sensing sheath, and determine a second strain of the strain-sensing sheath at the second location based on fluorescence spectroscopy of a second strain-sensing molecule associated with the strain-sensing sheath, and the controller further configured to:

determine a first local curvature of the luminal sample relative to the catheter between the first location and the second location based on determining the first position and the second position of the catheter relative to the luminal sample, determine a second local curvature of the catheter between the first location and the second location based on determining the first strain and the second strain of the strain-sensing sheath, and perform a three-dimensional (3D) reconstruction of the luminal sample.

2. The apparatus of claim 1, wherein performing the 3D reconstruction of the luminal sample includes segmenting one or more images generated by the structural imaging system and creating a curvature map from the first and second location of the luminal sample.

3. The apparatus of claim 2, wherein the one or more images are generated while helically moving the lens through the strain-sensing sheath along the luminal sample.

4. The apparatus of claim 1, wherein a first fluorescence spectrum obtained from the first location includes a first angular and first lateral location, and a second fluorescence spectrum obtained from the second location includes a second angular and second lateral location.

5. The apparatus of claim 2, wherein the curvature map is converted to a 3D catheter centerline by solving modified Frenet-Serret equations.

6. The apparatus of claim 5, wherein the one or more images are superimposed on the catheter's centerline and converted to a 3D mesh.

7. The apparatus of claim 1, wherein the structural imaging system comprises an optical coherence tomography (OCT) system.

8. The apparatus of claim 1, wherein the strain-sensing sheath comprises a sheath wall.

9. The apparatus of claim 8, wherein the first and second strain-sensing molecules are associated with the sheath wall.

10. The apparatus of claim 9, wherein the first and second strain-sensing molecules are associated with an inside face of the sheath wall.

11. The apparatus of claim 9, wherein the first and second strain-sensing molecules are embedded within the sheath wall.

12. The apparatus of claim 9, wherein the first and second strain-sensing molecules are associated with an outside face of the sheath wall.

13. The apparatus of claim 12, wherein the first and second strain-sensing molecules are associated with a plurality of wires attached to the outside face of the sheath wall.

14. The apparatus of claim 9, wherein the first and second strain-sensing molecules comprise single-walled carbon nanotubes (SWCNTs).

15. The apparatus of claim 1, wherein the controller, when determining the first strain, is further configured to:
transmit a first light towards the strain-sensing sheath,
obtain a second light from the strain-sensing sheath, and
determine the first strain based on obtaining the second light, and wherein the controller, when determining the second strain, is further configured to:
transmit a third light towards the strain-sensing sheath,
obtain a fourth light from the strain-sensing sheath, and
determine the second strain based on obtaining the fourth light.

16. The apparatus of claim 15, wherein the controller, when determining the first strain, is further configured to:
determine the first strain based on detecting a spectral shift in the second light, and wherein the controller, when determining the second strain, is configured to:
determine the second strain based on detecting a spectral shift in the fourth light.

17. The apparatus of claim 1, wherein the controller, when determining the first strain, is further configured to:
determine the first strain based on at least one of Raman spectroscopy or absorption spectroscopy, and wherein the controller, when determining the second strain, is further configured to:
determine the second strain based on at least one of Raman spectroscopy or absorption spectroscopy.

18. The apparatus of claim 1, wherein the strain-sensing system and the structural imaging system are optically coupled to the catheter by a rotary junction.

19. The apparatus of claim 1, wherein the luminal sample comprises a coronary artery.

* * * * *